United States Patent [19]
Slongo et al.

[11] Patent Number: 5,376,710
[45] Date of Patent: Dec. 27, 1994

[54] COMPOSITIONS STABILIZED BY O-HYDROXYPHENYL-1,3,5-TRIAZINES AND STERICALLY HINDERED AMINES

[75] Inventors: Mario Slongo, Tafers; Jean-Luc Birbaum, Fribourg; Jean Rody, Riehen, all of Switzerland; Andreas Valet, Eimeldingen, Germany

[73] Assignee: Ciba-Geigy Corporation, Ardsley, N.Y.

[21] Appl. No.: 29,213

[22] Filed: Mar. 10, 1993

Related U.S. Application Data

[62] Division of Ser. No. 685,367, Apr. 15, 1991, Pat. No. 5,229,512.

[30] Foreign Application Priority Data

Apr. 20, 1990 [CH] Switzerland .................. 1338/90

[51] Int. Cl.$^5$ ................................. C08K 5/34
[52] U.S. Cl. ................................. 524/87; 524/89; 524/91; 524/92; 524/94; 524/95; 524/99; 524/100; 524/102
[58] Field of Search ............... 524/95, 99, 100, 102, 524/87, 89, 91, 92, 94; 544/180, 198, 204, 209, 212, 215, 216, 219; 546/184, 186, 187, 188, 189, 208, 245

[56] References Cited

U.S. PATENT DOCUMENTS

| | | | |
|---|---|---|---|
| 3,896,125 | 7/1975 | Helmo et al. | 344/211 |
| 4,289,686 | 9/1981 | Rody et al. | 524/100 |
| 4,481,315 | 11/1984 | Rody et al. | 524/89 |
| 4,619,956 | 10/1986 | Susi | 524/87 |
| 4,740,542 | 4/1988 | Susi | 524/87 |
| 5,021,478 | 6/1991 | Rairchandran et al. | 524/91 |

OTHER PUBLICATIONS

Rogers et al Chemical Abstract, 73(261, 131684f, 1970).

Primary Examiner—Mukund J. Shah
Assistant Examiner—Y. N. Gupta
Attorney, Agent, or Firm—Luther A. R. Hall

[57] ABSTRACT

Compounds which comprise at least one group of the formula I or II

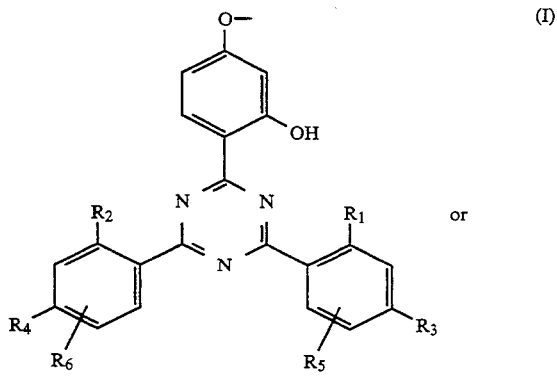

and at least one polyalkylpiperidine group of the formula III

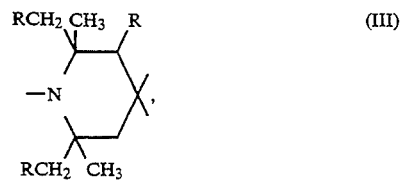

in which R and $R_1$ to $R_6$ have the meaning indicated in claim 1, are effective stabilizers for organic materials against damage by light, oxygen and heat.

16 Claims, No Drawings

COMPOSITIONS STABILIZED BY O-HYDROXYPHENYL-1,3,5-TRIAZINES AND STERICALLY HINDERED AMINES this is a divisional of application Ser. No. 07/685,367, filed on Apr. 15, 1991, now U.S. Pat. No. 5,229,512, issued on Jul. 20, 1993.

The present invention relates to novel compounds formed from o-hydroxyphenyl-1,3,5-triazines and sterically hindered amines, to their use for stabilising organic materials and to the organic materials stabilised using the novel compounds.

U.S. Pat. No. 4,619,956 describes the use of synergistic mixtures of a 2,2,6,6-tetraalkylpiperidine compound, its acid salts or complexes with metals and certain o-hydroxyphenyl-s-triazines for stabilising polymer films, coatings and moulded articles.

Compounds which contain at least one 2-(2'-hydroxyphenyl)benzotriazole or 2-hydroxybenzophenone group and at least one polyalkylpiperidine group in their molecule are known as light stabilisers from U.S. Pat. No. 4,289,686.

The invention relates to novel compounds comprising at least one group of the formula I or II

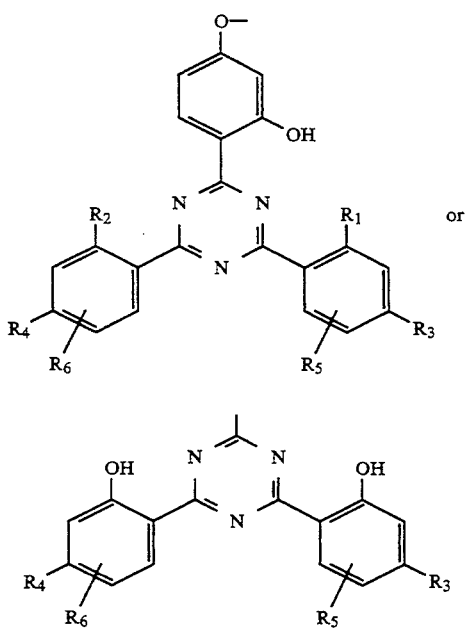

and at least one polyalkylpiperidine group of the formula III

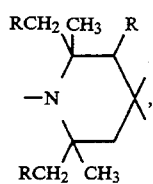

in which R is hydrogen or methyl, $R_1$ and $R_2$ independently of one another are hydrogen, —OH, $C_1$-$C_{12}$alkyl or halogen, $R_3$ and $R_4$ independently of one another are hydrogen, OH, $C_1$-$C_{12}$alkyl, $C_1$-$C_{18}$alkoxy, halogen or a radical comprising a group of the formula III and $R_5$ and $R_6$ independently of one another are hydrogen, $C_1$-$C_{12}$alkyl, halogen or a radical comprising a group of the formula III, with the proviso that possible substituents in the 1-position of the piperidine ring are not bonded to the nitrogen atom via —O— if the O atom in groups of the formula I is bonded to a bridging member —$CH_2CO$—.

Preferred compounds are those of the formula Ia or IIa

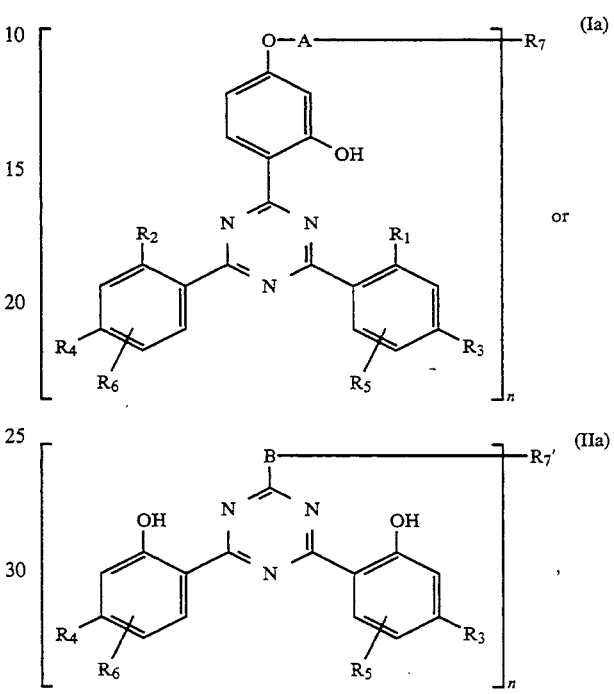

in which n is 1 or 2, $R_1$ and $R_2$ have the previously indicated meaning, $R_3$ and $R_4$ independently of one another are hydrogen, —OH, $C_1$-$C_{12}$alkyl, $C_1$-$C_{18}$alkoxy, halogen or a radical —O—A—$R_7$, $R_5$ and $R_6$ independently of one another are hydrogen, $C_1$-$C_{12}$alkyl, halogen or a radical —O—A—$R_7$, A is a direct bond, —$(CH_2)_mCO$— where m=zero or 1 to 4, —$CH_2CH(R')O$— or —$CH_2CH(OH)CH_2$—, B is a direct bond, —$(CH_2)_sCO$— where s=1 to 4 or —$(CH_2)_r$— where r=1 or 2, R' is hydrogen, methyl or phenyl, $R_7$ is a mono- or divalent radical comprising at least one polyalkylpiperidine group of the formula III and $R_7'$ can have the same meaning as $R_7$ or is the divalent radical of a diamine or diol, where in the latter case at least one of the radicals $R_3$ to $R_6$ in formula IIa is a group —O—A—$R_7$, with the proviso that possible substituents in the 1-position of the piperidine ring are not bonded to the N atom via —O— if A is —$CH_2CO$—.

Here and in the following, the bond line on the left in divalent radicals, such as —$CH_2CH(R')O$— or —$(CH_2)_s$—$CO$—, is the linkage to the symbol or atom on the left thereof.

m and s are preferably 1. A is preferably —$CH_2CH(OH)CH_2$— and in particular —$CH_2CO$—. B is preferably a direct bond or —$CH_2CO$—. R is preferably hydrogen and R' is in particular hydrogen or methyl.

Examples of suitable radicals $R_7$ or $R_7'$ comprising at least one group of the formula III which may be mentioned are the following classes:

if n=1

1. Radicals of the Formula IV

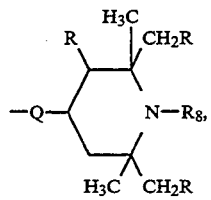

in which R has the abovementioned meaning, $R_8$ is hydrogen, oxy, $C_1$-$C_{12}$alkyl, $C_1$-$C_{12}$alkoxy, $C_3$-$C_8$alkenyl, $C_3$-$C_8$alkenyloxy, $C_3$-$C_8$alkynyl, $C_5$-$C_6$cycloalkyl, $C_5$-$C_6$cycloalkyloxy, phenyl—$C_1$-$C_4$alkyl, $C_1$-$C_8$alkanoyl, $C_3$-$C_5$alkenoyl, —CH$_2$CH(OH)R' or phenoxy, R' is hydrogen, methyl or phenyl, Q is —O—$C_2$-$C_{12}$alkylene or —NR$_9$—$C_2$-$C_{12}$alkylene if A or B has the meaning indicated, but A is not equal to a direct bond or —CH$_2$CH(R')O—, or in compounds of the formula Ia Q is $C_2$-$C_{12}$alkylene if A is a direct bond or —CH$_2$CH(R')O—, or is a direct bond if A is —CH$_2$CH(R')O—, $R_9$ is hydrogen, $C_1$-$C_{18}$alkyl, allyl, $C_5$-$C_6$cycloalkyl, phenyl—$C_1$-$C_4$alkyl, $C_3$-$C_{18}$alkyl interrupted by one or more —O— or a group of the formula IIIa

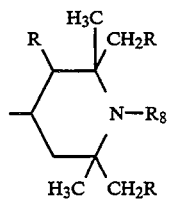

2. Radicals of the Formula V

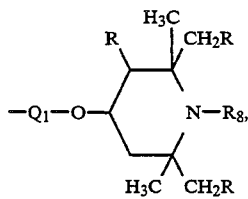

in which $Q_1$ is a direct bond, —O—$C_2$-$C_{12}$alkylene or —NR$_9$—$C_2$-$C_{12}$ alkylene if A or B has the meaning indicated, but A is not equal to a direct bond or —CH$_2$CH(R')O—, or in compounds of the formula Ia $Q_1$ is $C_2$-$C_{12}$alkylene if A is a direct bond or —CH$_2$CH(R')O—, or —OCO—$C_2$-$C_{12}$alkylene if A in compounds of the formula Ia is —CH$_2$CH(OH)CH$_2$— or B in formula IIa is —(CH$_2$)$_r$—, and R, $R_8$ and $R_9$ have the abovementioned meaning.

3. Radicals of the Formula VI

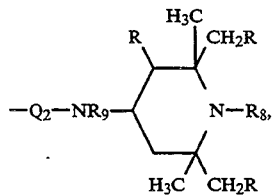

in which R, $R_8$ and $R_9$ have the abovementioned meaning, $Q_2$ is a direct bond or —NR$_9$—$C_2$-$C_{12}$alkylene if A or B have the abovementioned meaning, but A is not equal to a direct bond or —CH$_2$CH(R')O—, or in compounds of the formula Ia $Q_2$ is —CO—$C_2$-$C_{12}$alkylene if A is a direct bond or —CH$_2$CH(R')O—, or is —O—CO—$C_1$-$C_{12}$alkylene or —OCO—$C_1$-$C_{12}$alkylene—CO— if A in formula Ia is —CH$_2$CH(OH)CH$_2$— or B in formula IIa is —(CH$_2$)$_r$—.

4. Radicals of the Formula VIIa in Compounds of the Formula Ia

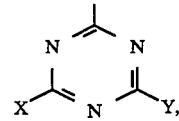

where A is a direct bond or —CH$_2$CH(R')O—, or radicals of the formula VIIb in compounds of the formula Ia or IIa

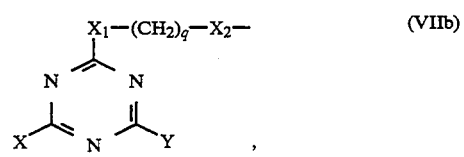

where A or B has the meaning indicated, but A is not equal to a direct bond or —CH$_2$CH(R')O—, and in which q is 2–12, in particular 2–4, and $X_1$ and $X_2$ independently of one another are —O— or —R$_9$N—,

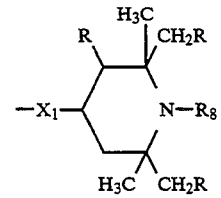

and Y has the same meaning as X or is $C_1$-$C_{18}$alkoxy or —NR$_9$R$_{10}$, R, $R_8$ and $R_9$ have the abovementioned meaning and $R_{10}$ can have the same meaning as $R_9$ or, together with $R_9$ and the bonding N atom, forms a 5- or 6-membered heterocyclic ring.

5. Radicals of the Formula VIII

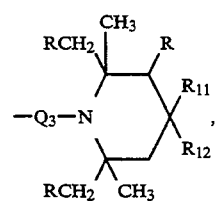

in which $Q_3$ is a direct bond if A in formula Ia is —CH$_2$CH(OH)CH$_2$— or B in formula IIa is a direct bond or —(CH$_2$)$_r$—, or $Q_3$ is —OCH(R')CH$_2$— if A or B has the meaning indicated, but A is not equal to a direct bond or —CH$_2$CH(R')O—, or $Q_3$ in compounds of the formula Ia is —CH(R')CH$_2$— if A is a direct bond or —CH$_2$CH(R')O—, $R_{11}$ is hydrogen, $C_1$-$C_{18}$alkoxy, $C_3$-$C_8$alkenyloxy or benzyloxy and $R_{12}$ can have the same meaning as $R_{11}$ or $R_{11}$ and $R_{12}$ together are —O—$C_2$-$C_8$alkylene—O—, or if $R_{11}$=H, $R_{12}$ is —OH or —NR$_9$—CO—R$_{13}$, in which $R_9$ has the abovementioned meaning and $R_{13}$ is $C_1$-$C_{18}$alkyl, $C_2$-$C_4$alkenyl or phenyl.

6. Radicals of the Formula IX

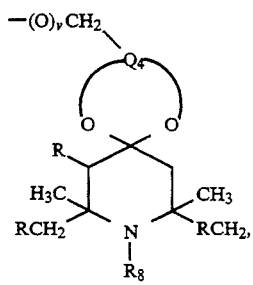

in which $Q_4$ is $C_2$-$C_8$alkylene, in particular

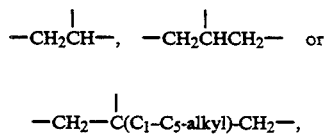

and v is the number 1 if A or B have the meaning indicated, but A is not equal to a direct bond or —CH$_2$CH(R')O—, or v in compounds of the formula Ia is zero if A is a direct bond or —CH$_2$CH(R')O—, and R and $R_8$ have the abovementioned meaning.

7. Radicals of the formula Xa or Xb

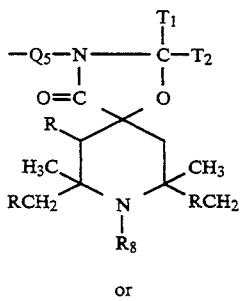

or

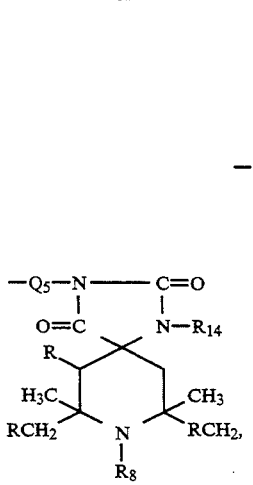

in which $Q_5$ is —OCH$_2$CH$_2$— or —OCH$_2$CH(OH)CH$_2$— if A or B has the meaning indicated, but A is not equal to a direct bond or —CH$_2$CH(R')O—, or in compounds of the formula Ia $Q_5$ is —CO(CH$_2$)$_2$— or —CO(CH$_2$)$_3$— if A is a direct bond or —CH$_2$CH(R')O—, $Q_5$ is a direct bond if A is —CH$_2$CH(OH)CH$_2$—, or $Q_5$ is —OCO(CH$_2$)$_s$— where s=1–4 if A in formula Ia is —CH$_2$CH(OH)CH$_2$— or B in formula IIa is —(CH$_2$)$_r$—, $T_1$ an $R_2$ independently of one another are hydrogen, $C_1$-$C_{18}$alkyl, phenyl—$C_1$-$C_4$alkyl or phenyl or naphthyl which are unsubstituted or substituted by halogen or $C_1$-$C_4$alkyl, or $T_1$ and $T_2$, together with the C atom bonding them, form a $C_5$-$C_{12}$cycloalkane ring, R and $R_8$ have the abovementioned meaning and $R_{14}$ is hydrogen, $C_1$-$C_{12}$alkyl, allyl, benzyl or $C_2$-$C_6$alkoxyalkyl.

if n=2

8. Radicals of the Formula XI

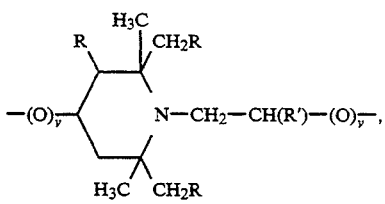

in which v is the number 1 if A or B have the meaning indicated, but A is not equal to a direct bond or —CH$_2$CH(R')O—, or v in compounds of the formula Ia is zero if A is a direct bond or —CH$_2$CH(R')O—, and R and R' have the abovementioned meaning.

9. Radicals of the Formula XII

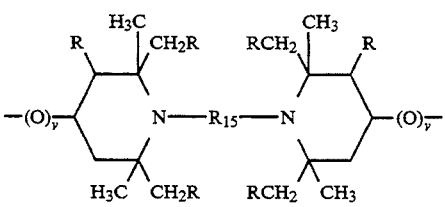

in which the abovementioned applies for v and R and $R_{15}$ is $C_2$-$C_{12}$alkylene which can be interrupted by one or more O atoms, —CH$_2$CH=CHCH$_2$—, xylylene or $\text{—[CH}_2\text{CH(OH)CH}_2\text{O(CH}_2)_{t/2}]_2$ where t=1–6.

10. Radicals of the Formula XIII

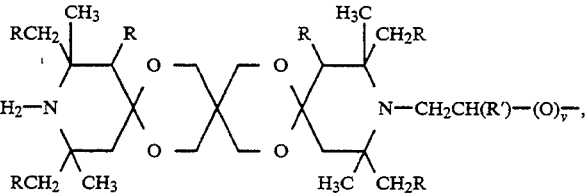

in which the abovementioned applies to v, R and R'.

11. Radicals of the Formula XIV

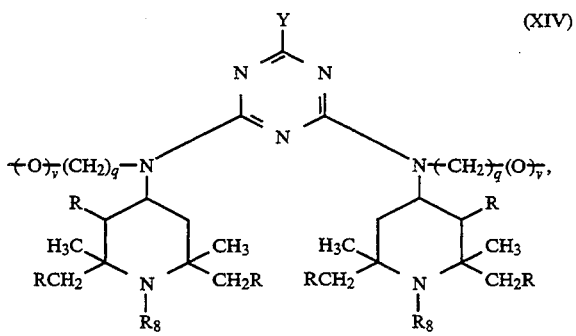 (XIV)

in which the abovementioned applies to Y, q, v, R and $R_8$.

12. Radicals of the Formula XV

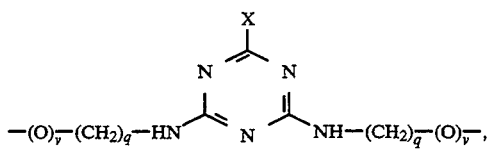 (XV)

in which the abovementioned applies to q, v and X.

13. Radicals of the Formulae XVIa and XVIb

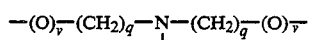 (XVIa)

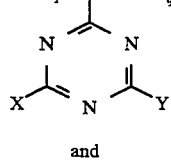

and

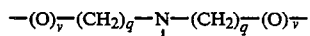 (XVIb)

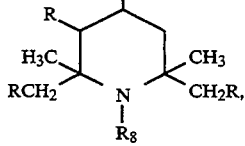

in which the abovementioned applies to q, v, X and Y.

14. Radicals of the Formula XVIIa in compounds of the formula Ia

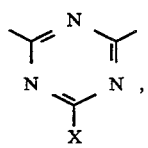 (XVIIa)

where A is a direct bond or —CH$_2$CH(R')O—, or radicals of the formula XVIIb in compounds of the formula IIa

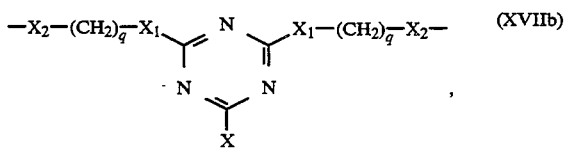 (XVIIb)

where A or B has the meaning indicated, but A is unequal to a direct bond or —CH$_2$CH(R')O—, and in which q, X, $X_1$ and $X_2$ have the abovementioned meaning.

15. Radicals of the Formula XVIII in Compounds of the Formula Ia or IIb in which A and B have the Meaning Indicated, but A is Unequal to a Direct Bond or —CH$_2$CH(R')O—

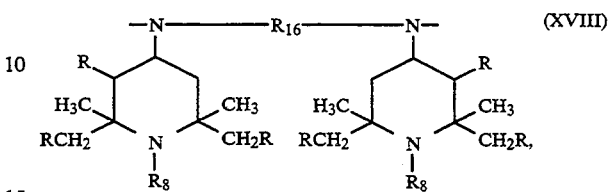 (XVIII)

in which R and $R_8$ have the abovementioned meaning and $R_{16}$ is $C_2$–$C_{12}$alkylene, phenylene, naphthylene, biphenylene, xylylene, a group —CH$_2$CH(OH)CH$_2$—, the divalent radical of an aliphatic, cycloaliphatic or aromatic dicarboxylic acid or —CO—.

16. $R_7'$ in Compounds of the Formula IIa can Additionally be a Radical of the Formula XIX —$X_1$—$R_{16}$—$X_2$— (XIX) in which $X_1$, $X_2$ and $R_{16}$ have the abovementioned meaning.

Alkyl, alkoxy, alkenyl, alkynyl, alkanoyl, alkenoyl, alkenyloxy, alkylene or alkenylene groups represented by any radicals can be straight-chain or branched. The groups mentioned are preferably straight-chain.

Examples of alkyl groups $R_2$ to $R_6$, $R_8$ and $R_{14}$ are methyl, ethyl, n-propyl, isopropyl, n-, sec- and tert-butyl, n-pentyl, n-hexyl, 2-ethylhexyl, 2-methylpentyl, n-heptyl, n-octyl, n-nonyl, n-decyl and n-dodecyl; $R_9$, $R_{10}$, $R_{13}$, $T_1$ and $T_2$ as $C_1$–$C_{18}$alkyl, can additionally be n-tetradecyl, n-hexadecyl or n-octadecyl.

Alkyl groups $R_1$ to $R_6$ are preferably straight-chain and have 1–C atoms. $R_8$ in the meaning of alkyl is particular $C_1$–$C_8$alkyl and especially $C_1$–$C_4$alkyl.

Alkyl groups $R_9$, $R_{10}R_{13}$, $T_1$ and $T_2$ preferably have 1–12, particularly 1–8 and especially 1–4 C atoms. The ethyl and especially methyl groups mentioned are particularly preferred.

Examples of alkoxy groups $R_3$, $R_4$, $R_8$, $R_{11}$, $R_{12}$ and Y having up to 12 or 18 C atoms are methoxy, ethoxy, n- and isopropyloxy, n-, sec- and tert-butyloxy, n-pentyloxy, n-hexyloxy, n-heptyloxy, n-octyloxy, n-decyloxy, n-dodecyloxy, n-tetradecyloxy, n-hexadecyloxy and n-octadecyloxy. These alkoxy groups preferably have 1–12 and in particular 1–4 C atoms. Ethoxy and in particular methoxy groups are very particularly preferred.

If any substituents are alkylene groups or if these substituents contain alkylene moieties, these are preferably straight-chain alkylene preferably having 2 to 12 C atoms.

If any substituents contain phenylene, naphthylene or biphenylene groups, they are, for example, o-, m- or p-phenylene, 1,4-naphthylene or 4,4'-biphenylene.

If $R_1$ to $R_6$ are halogen, they are in particular chlorine or bromine.

$R_1$ and $R_2$, $R_3$ and $R_4$ and $R_5$ and $R_6$ in pairs preferably each have the same meaning. Preferably, $R_1$ and $R_2$ and $R_3$ and $R_4$ in pairs are each hydrogen or $C_1$–$C_4$alkyl and $R_5$ and $R_6$ are each hydrogen. In formula I and Ia, $R_1$ and $R_2$ or $R_3$ and $R_4$ are in particular each hydrogen, —OH or methyl. In formula II and IIa, $R_3$ and $R_4$ are preferably hydrogen, alkoxy having 1–8 and in particular 1–4 C atoms or a radical —O—A—$R_7'$, especially

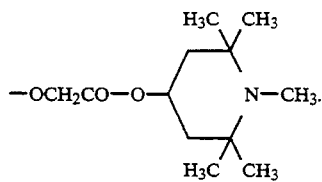

$R_5$ and $R_6$ are preferably hydrogen. $R_1$ and $R_2$ in formula I or Ia are particularly preferably each hydrogen or methyl and $R_3$ and $R_4$ are preferably each hydrogen and in particular each methyl.

$R_8$ as alkyl or alkoxy preferably has 1–8 and in particular 1–4 C atoms. If $R_8$ is $C_3$–$C_8$alkenyl or $C_3$–$C_8$alkenyloxy, it is, for example, 1-propenyl, allyl, methallyl, 2-butenyl, 2-pentenyl, 2-hexenyl, 2-octenyl or 4-tert-butyl-2-butenyl or the corresponding alkenyloxy radicals. $R_8$ as $C_3$–$C_8$alkynyl is preferably propargyl. $C_5$–$C_6$Cycloalkyl or $C_5$–$C_6$cycloalkoxy groups $R_8$ are in particular cyclohexyl or cyclohexyloxy. $C_1$–$C_8$Alkanoyl $R_8$ is, for example, formyl, propionyl, isobutyryl, hexanoyl or octanoyl, preferably acetyl. $C_3$–$C_9$Alkenoyl is preferably acryloyl or methacryloyl. If $R_8$, $R_9$ or $R_{10}$ are phenyl—$C_1$–$C_4$alkyl, phenylethyl and especially benzyl are in particular suitable.

$R_8$ is preferably hydrogen, oxy, $C_1$–$C_{12}$alkyl, $C_3$–$C_8$alkenyl, $C_3$–$C_8$alkynyl, phenyl—$C_1$–$C_4$alkyl, $C_1$–$C_8$alkanoyl, $C_3$–$C_8$alkenoyl or —$CH_2CH(OH)R'$. $R_8$ is particularly preferably hydrogen, oxy, $C_1$–$C_8$, particularly $C_1$–$C_4$alkyl, allyl, benzyl, acetyl or acryloyl and in particular hydrogen, methyl, allyl, benzyl or acetyl. Hydrogen and methyl are very particularly preferred.

Alkyl groups $R_9$ and $R_{10}$ preferably have 1–12, in particular 1–8 and especially 1–4 C atoms. Ethyl and especially methyl are very particularly preferred. If $R_9$ or $R_{10}$ is $C_5$–$C_6$cycloalkyl, it is in particular cyclohexyl. As $C_3$–$C_{18}$alkyl which is interrupted by one or more O atoms, $R_9$ and $R_{10}$ are, for example, —$CH_2CH_2OCH_3$, —$CH_2OCH_2CH_3$, —$CH_2CH_2OC_4H_9$ or —$CH_2CH_2OCH_2CH_2CH_3$.

$R_9$ and $R_{10}$ are preferably independently of one another hydrogen, $C_1$–$C_8$ and in particular $C_1$–$C_4$alkyl, especially ethyl or methyl, allyl, cyclohexyl, benzyl or a group of the formula IIIa in which R is hydrogen and $R_8$ has the abovementioned preferred meaning. $R_9$ and $R_{10}$ are particularly preferably each H or $C_1$–$C_4$alkyl, very particularly preferably each hydrogen.

Of the radicals of the formula IV, those are preferred in which Q is —$OCH_2CH_2$— or —$NHCH_2CH_2$— or in the case of A=—$CH_2CH(R')O$— is a direct bond, R is hydrogen and $R_8$ has the abovementioned preferred meaning and is especially hydrogen or methyl. Examples of compounds containing such radicals are:

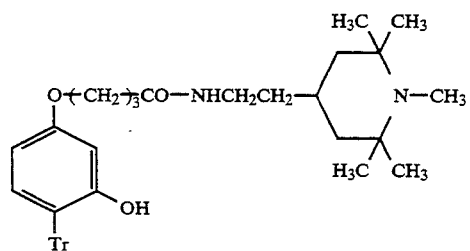

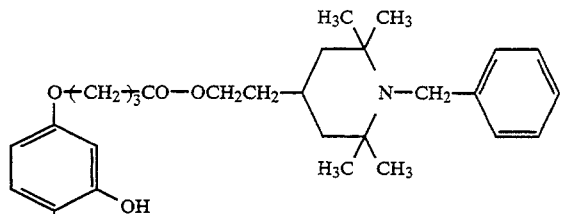

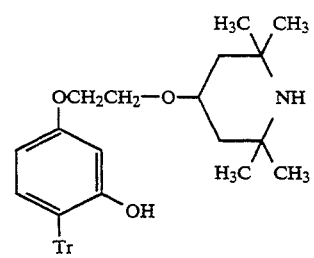

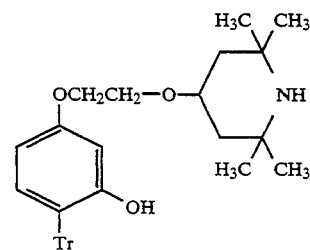

where Tr here and in the following is a group of the formula

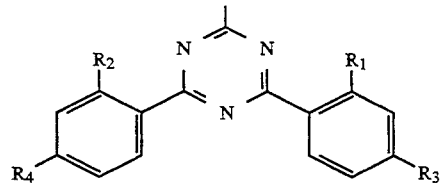

where $R_1=R_2=$H or methyl and $R_3=R_4=$H and in particular methyl.

As radicals of the formula V, those are preferred in which R is hydrogen, $Q_1$ is —NH—$C_2$–$C_4$alkylene or —O—$C_2$–$C_4$alkylene and in particular a direct bond and $R_8$ has the abovementioned preferred meaning. Examples of compounds of the formula Ia and IIa having radicals of the formula V are:

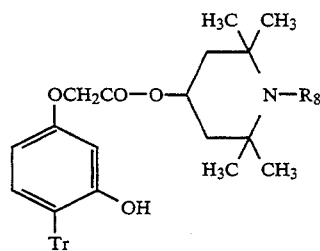

where $R_8=$H, methyl, benzyl, allyl or acetyl

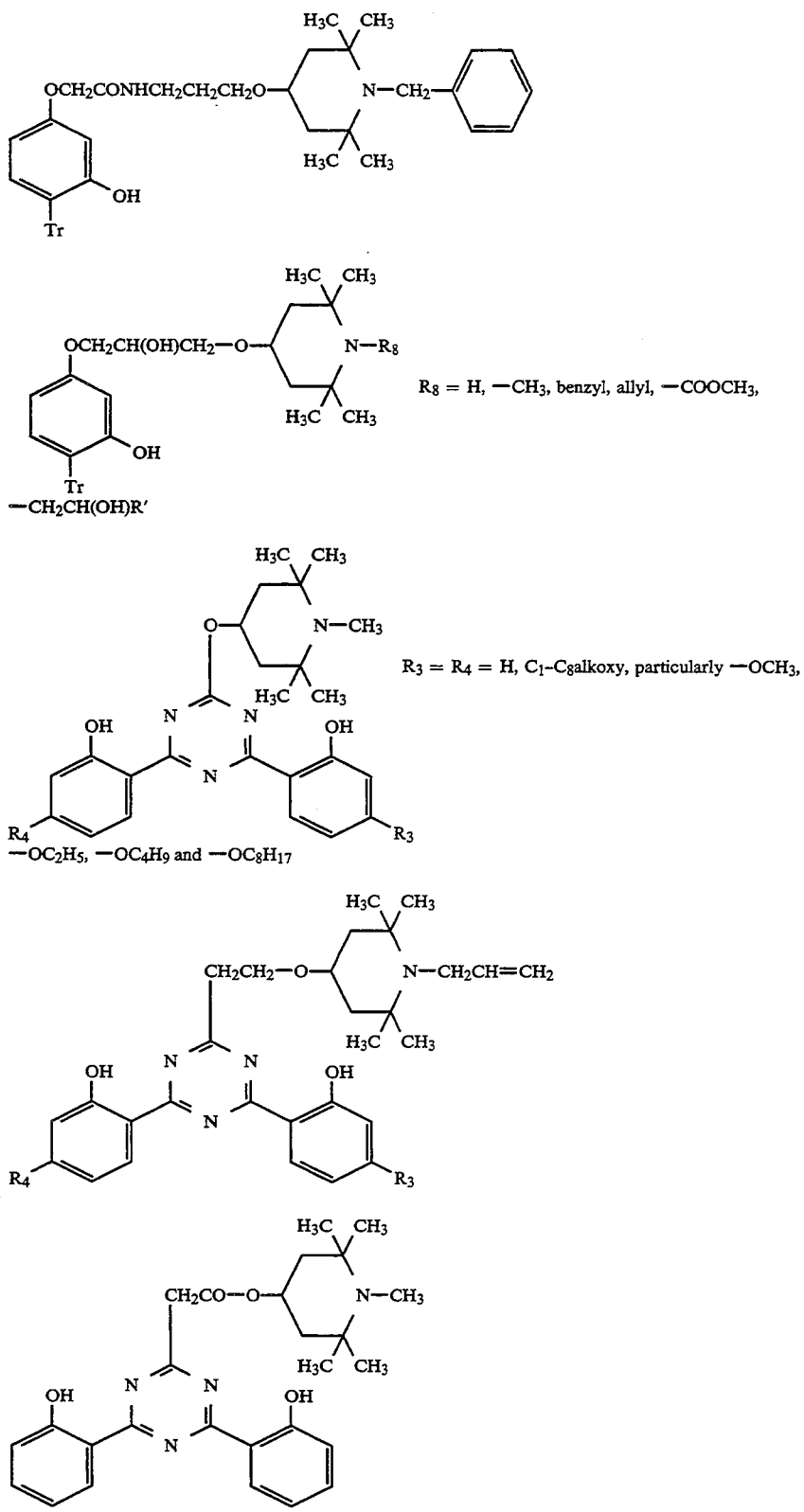

In preferred radicals of the formula VI R is hydrogen, $R_9$ is preferably $C_1$-$C_8$alkyl, in particular $C_1$-$C_4$alkyl and especially hydrogen, $Q_2$ is a direct bond or —$NR_9$—$C_2$-$C_4$alkylene or —OCO—$C_1$-$C_4$alkylene or —OCO—$C_2$-$C_4$alkylene—CO— (A=—$CH_2CH(OH)CH_2$— or B=—$(CH_2)_r$—) and $R_8$ has the abovementioned preferred meaning. Examples of radicals of this type of compounds of the formula Ia and IIa are:

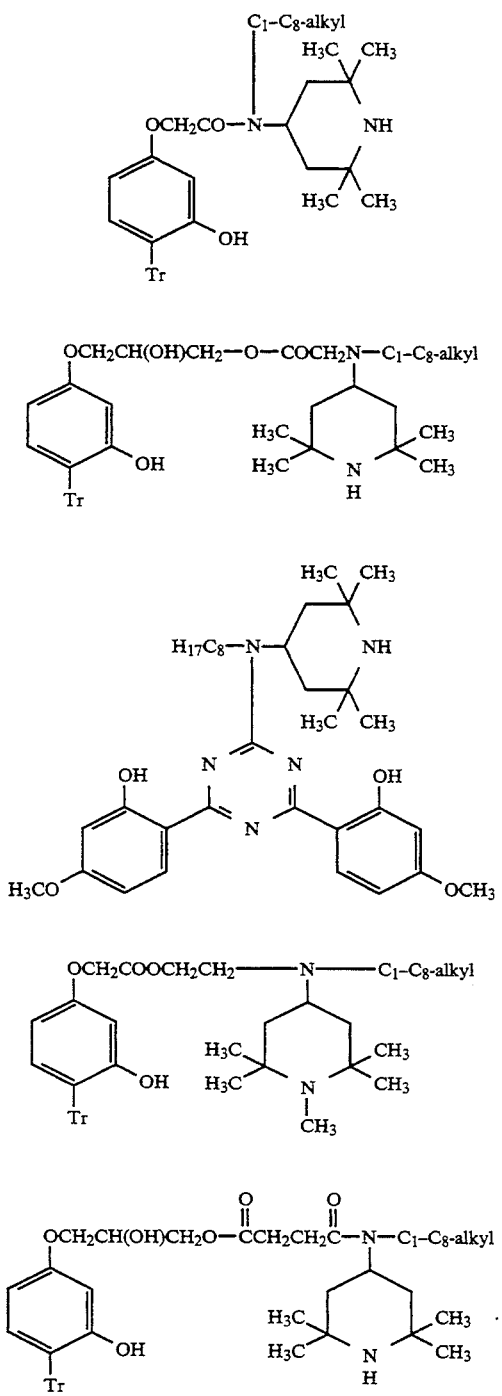

X in radicals of the formula VIIa and VIIb is preferably

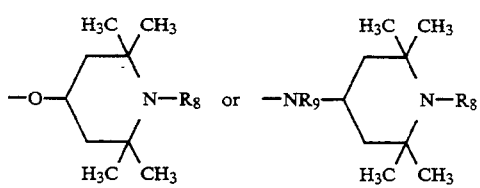

where $R_9$=H or $C_1$-$C_4$alkyl, where $R_8$ has the abovementioned preferred meaning.

Y preferably has the same meaning as X or is $C_1$-$C_8$, in particular $C_1$-$C_4$alkoxy, —$NR_9R_{10}$ where $R_9$ and $R_{10}$=independently of one another H, $C_1$-$C_8$— and in particular $C_1$-$C_4$alkyl, allyl, cyclohexyl or benzyl. If $R_9$ and $R_{10}$ together with the bonding C atom form a 5- or 6-membered ring, it is, for example, a pyrrolidine, piperidine, 2,6-dimethylpiperidine, piperazine, 4-methylpiperazine or morpholine ring. $X_1$ and $X_2$ in formula VIIb are preferably independently of one another —O— or —NH—.

Examples of compounds containing such triazine radicals which may be mentioned are:

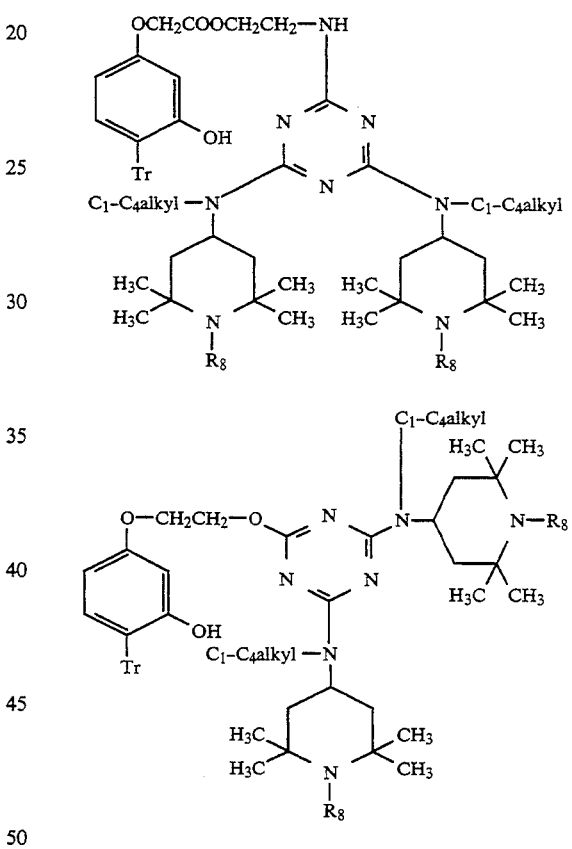

$R_8$=the abovementioned preferred meaning, in particular H or methyl.

Alkoxy groups $R_{11}$ and $R_{12}$ in formula VIII preferably have 1–8 and in particular 1–4 C atoms. As $C_3$-$C_8$alkenyloxy, the radicals mentioned are in particular allyloxy. If $R_{11}$ and $R_{12}$ together form a group —O—$C_2$-$C_8$alkylene—O—, it is, for example, —O—$CH_2C$-$H_2$—O—, —O—$CH_2CH_2CH_2$—O— or —O$CH_2CH$(-$C_1$-$C_5$alkyl)—$CH_2$—O—. $R_{13}$ as alkyl in particular has 1–8 and especially 1–4 C atoms. As $C_2$-$C_4$alkenyl, $R_{13}$ is, for example, vinyl or allyl. R is preferably hydrogen and $Q_3$ is preferably —OCH(R')$CH_2$— or a direct bond.

Examples of compounds of the formula Ia or IIa containing radicals of the formula VIII which may be mentioned are:

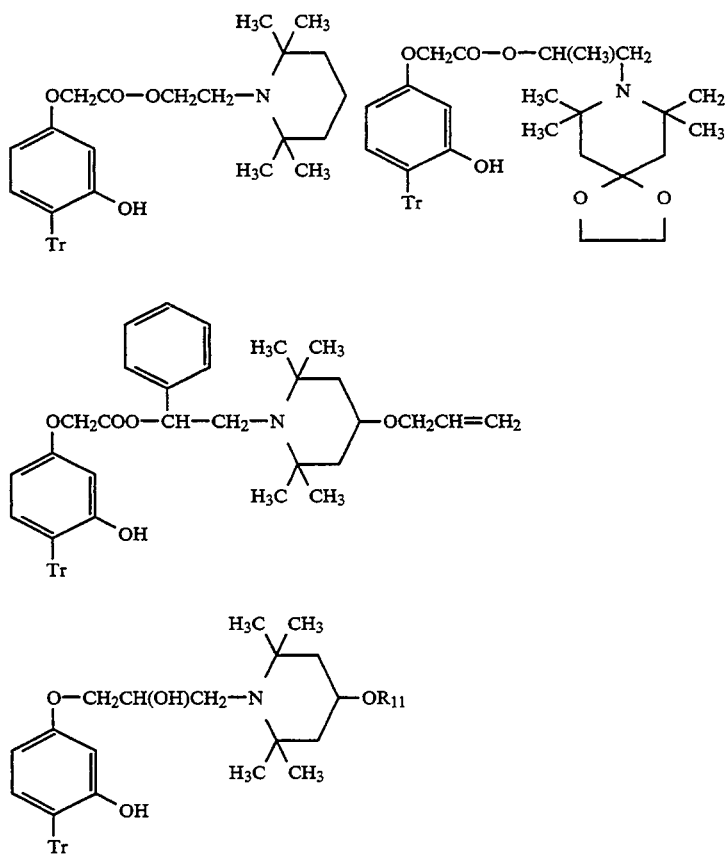

$R_{11}$=H, $C_1$-$C_{18}$alkyl, particularly $C_1$-$C_8$alkyl, very particularly methyl, allyl or benzyl.

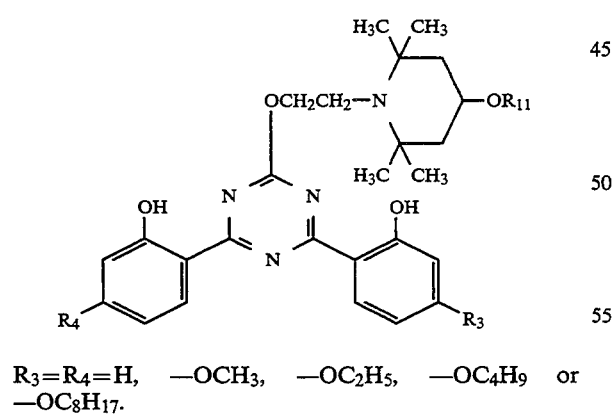

$R_3$=$R_4$=H, —OCH$_3$, —OC$_2$H$_5$, —OC$_4$H$_9$ or —OC$_8$H$_{17}$.

In the radicals of the formula IX, $Q_4$ is preferably $$-CH_2\overset{|}{CH}-,\ -CH_2\overset{|}{CH}CH_2-\ \text{or}\ -CH_2-\overset{|}{C}(C_2H_5)-CH_2-,$$

R is hydrogen and $R_8$ has the preferred meaning mentioned above. Examples of compounds of the formula Ia or IIa containing such radicals which may be mentioned are:

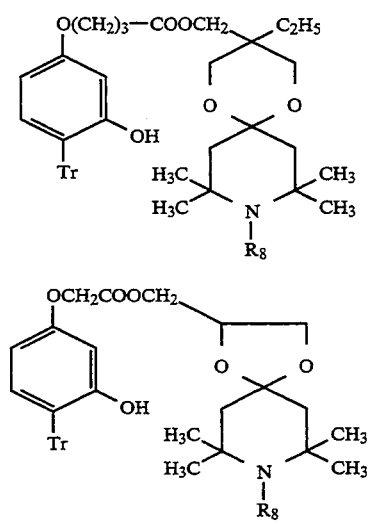

-continued

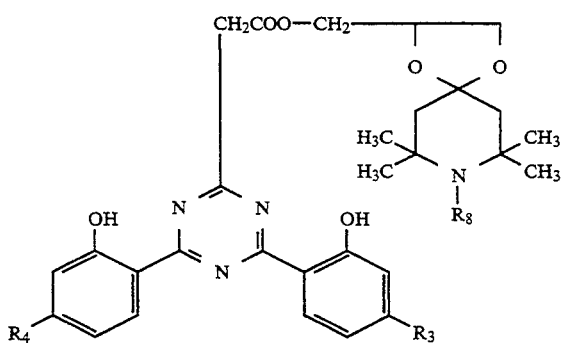

$R_8 = H$ or methyl, $R_3 = R_4 = H$ or $C_1$-$C_8$alkoxy.

In radicals of the formula Xa or Xb, R is preferably hydrogen and $R_8$ has the preferred meaning mentioned above. $R_{14}$ as $C_2$-$C_6$alkoxyalkyl is, for example, methoxymethyl, ethoxymethyl, propoxymethyl, tert-butoxymethyl, ethoxyethyl, ethoxypropyl or propoxypropyl, $R_{14}$ is preferably $C_1$-$C_4$alkyl, allyl or benzyl and in particular H. Alkyl groups $T_1$ and $T_2$ are preferably straight-chain and in particular have 1–4 C atoms. As phenyl-$C_1$-$C_4$alkyl, $T_1$ and $T_2$ are in particular phenylethyl and especially benzyl. If $T_1$ and $T_2$ together with the bonding C atoms form a cycloalkane ring, this can be, for example, a cyclopentane, cyclohexane, cyclooctane or cyclododecane ring. Preferably, $T_1$ and $T_2$ are hydrogen or they form a cyclododecane ring together with the bonding C atom.

Examples of compounds of the formula Ia or IIa containing such radicals which may be mentioned are:

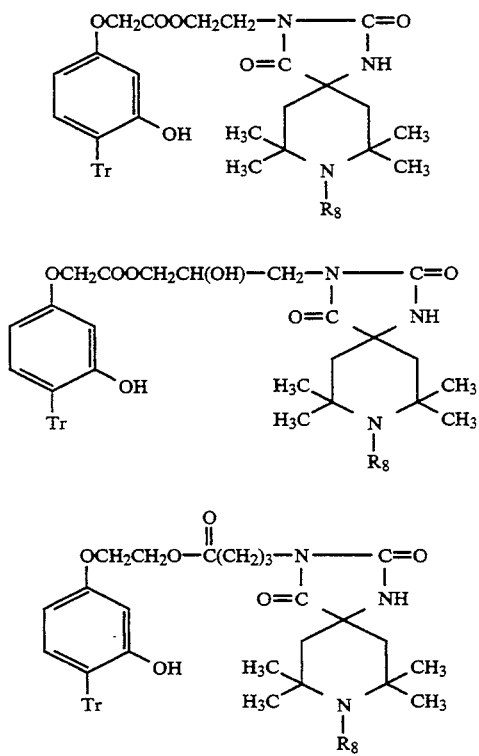

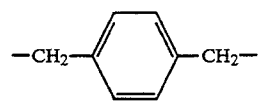

where $R_8 = H$ or methyl and $R_3 = R_4 = H$ or $C_1$-$C_8$alkoxy.

R in the formulae XI to XIX is preferably hydrogen and $R_8$ has the preferred meaning mentioned above. q in the radicals of the formulae XIV, XV, XVIa and XVIb is in particular 2. R' is preferably H or methyl and v is preferably the number 1.

$R_{15}$ in formula XII is preferably alkylene having 2–12 and in particular 2–6 C atoms, — $\pm CH_2CH(OH)CH_2O(CH_2)_{t/2}]_2$ where $t = 1–3$ and in particular 2, $$-CH_2-\!\!\bigcirc\!\!-CH_2-$$

or —$CH_2CH=CHCH_2$—. $R_{16}$ as phenylene, naphthylene or biphenylene is in particular m- or p-phenylene, 1,4-naphthylene or 4,4'-biphenylene. If $R_{16}$ is a divalent radical of an aliphatic, cycloaliphatic or aromatic dicarboxylic acid, it is, for example, a malonic acid, succinic acid, glutaric acid, adipic acid, suberic acid, sebacic acid, maleic acid, dibutylmalonic acid, dibenzylmalonic acid, itaconic acid, hexahydrophthalic acid, bicycloheptenedicarboxylic acid, phthalic acid, or iso- or terephthalic acid radical. $R_{16}$ is preferably straight-chain $C_2$-$C_{12}$alkylene. Y and X in the formulae XIV, XV, XVIa, XVIIa and XVIIb in particular have the preferred meanings mentioned under formula VIIa or VIIb.
Examples of compounds of the formula Ia or IIa containing radicals of the formulae XI to XIX which may be mentioned are:
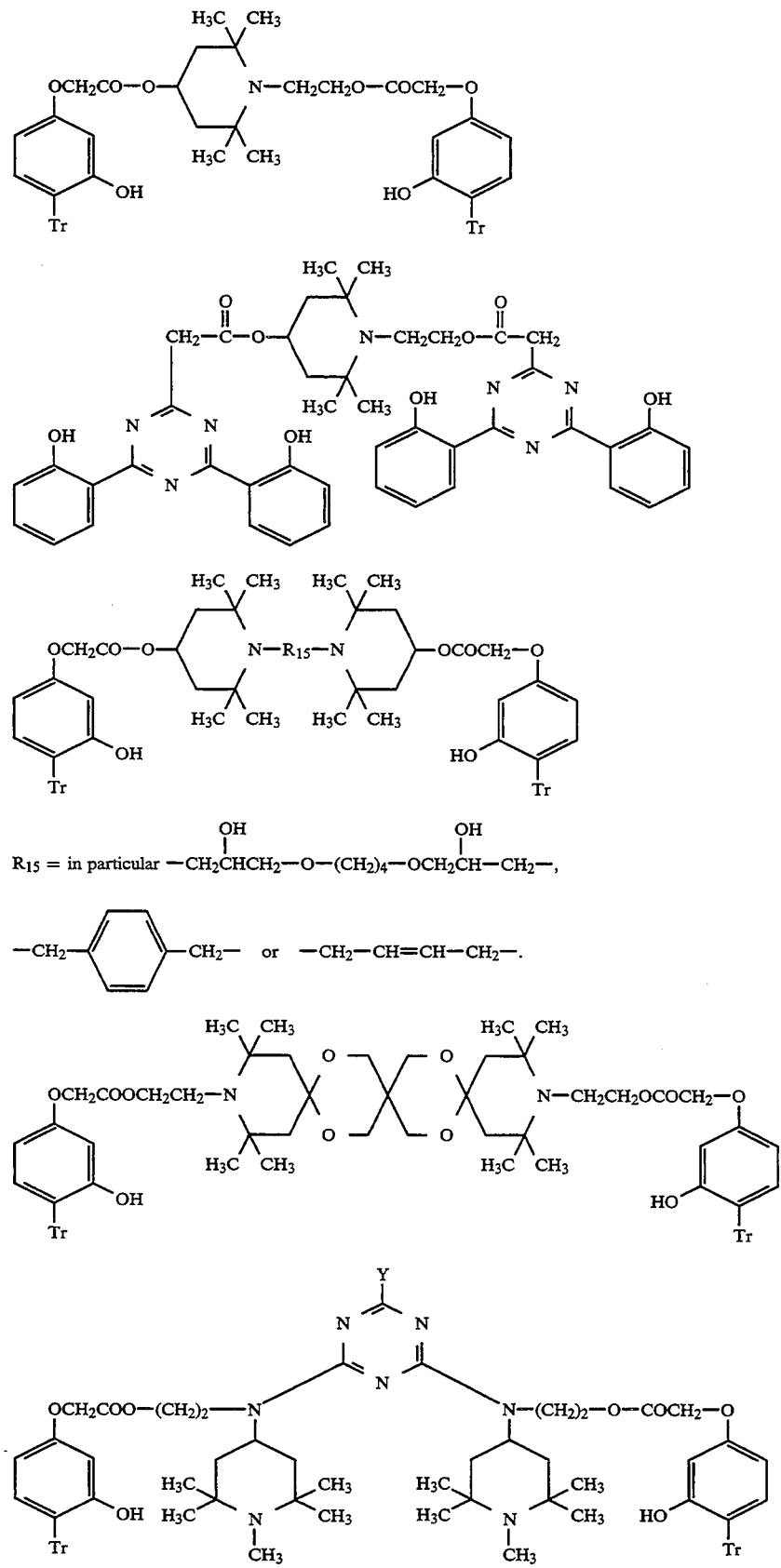

-continued
Y = $C_1$–$C_8$ alkoxy, —NH—$C_1$–$C_8$ alkyl, —N($C_1$–$C_8$ alkyl)$_2$, 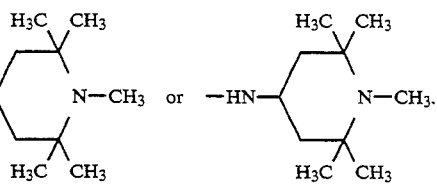
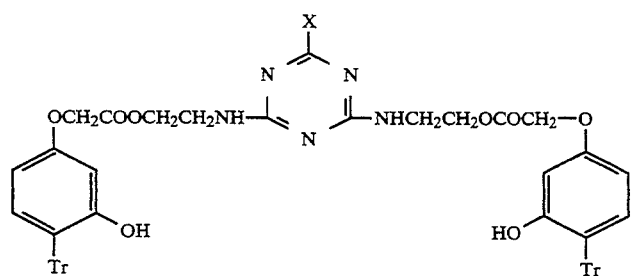
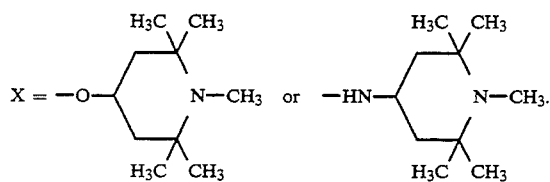
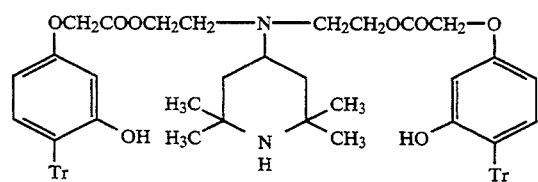
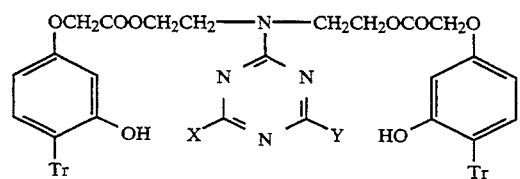
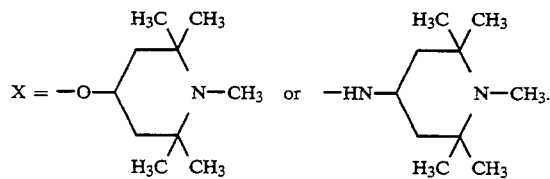
Y = the same meaning as X or $C_1$–$C_8$alkoxy, —NH-$C_1$–$C_8$alkyl, —N($C_1$–$C_8$alkyl)$_2$.
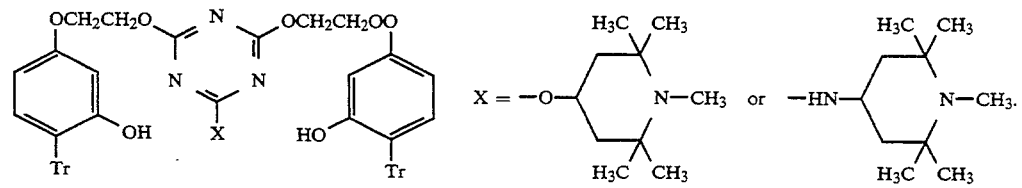

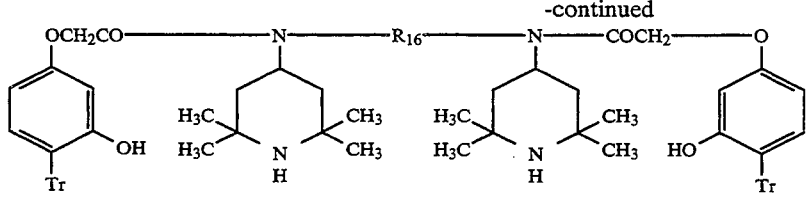

where $R_{16}$=straight-chain $C_2$-$C_{12}$alkylene.

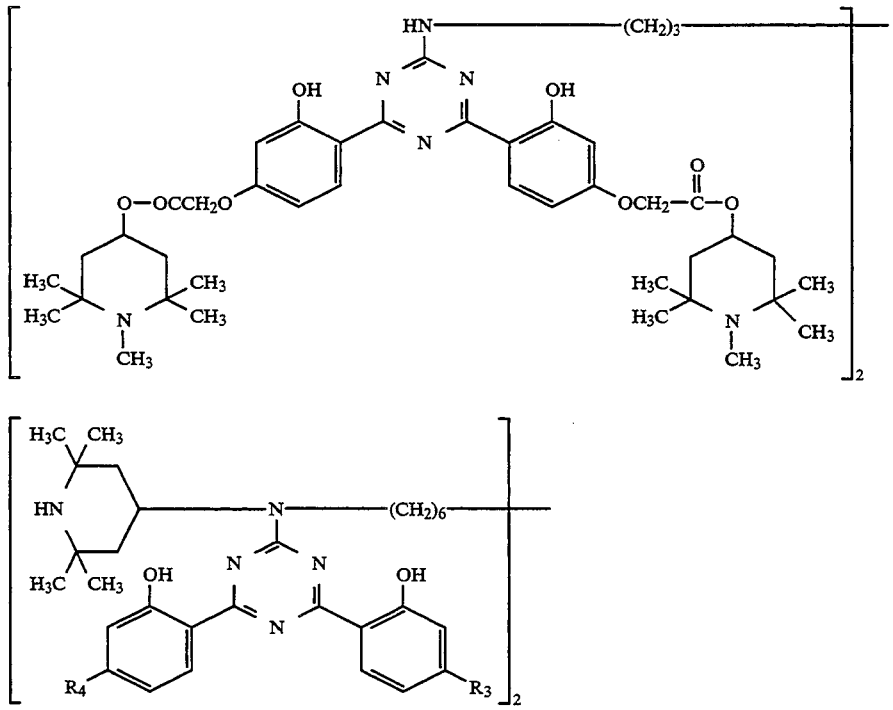

$R_3=R_4=H$ or $C_1$-$C_8$alkoxy.

Preferred compounds of the formula Ia and IIa are those in which A or B are —$CH_2CO$—, $R_1$ and $R_2$ and also $R_3$ and $R_4$ in pairs are each hydrogen or $C_1$-$C_4$alkyl, $R_5$ and $R_6$ are each hydrogen, $R_7$ and $R_7'$ are a radical of the formula V or XI, $Q_1$ is a direct bond, $R_8$ is hydrogen, $C_1$-$C_4$alkyl, benzyl, allyl, acetyl or acryloyl, v is the number 1 and $R'$ is hydrogen, methyl or phenyl.

Particularly preferred compounds of the formula IIa are those in which B is —$CH_2CO$—, $R_3$ and $R_4$ are each hydrogen or methyl, $R_5$ and $R_6$ are each hydrogen and $R_7'$ is a radical of the formula V, in which $Q_1$ is a direct bond and $R_8$ is hydrogen, methyl, benzyl, allyl or acetyl.

Very particularly preferred compounds of the formula Ia are those in which A is —$CH_2CO$—, $R_1$ and $R_2$ are each hydrogen and in particular each methyl, $R_3$ and $R_4$ are each methyl and $R_5$ and $R_6$ are each hydrogen and $R_7$ is a radical of the formula V or XI, in which $Q_1$ is a direct bond, $R_8$ is hydrogen, methyl, benzyl, allyl or acetyl, v is the number 1 and $R'$ is hydrogen or methyl.

Additionally preferred compounds of the formula Ia are those in which A is —$CH_2CH(OH)CH_2$—, $R_1$ and $R_2$ and also $R_3$ and $R_4$ in pairs are each hydrogen or $C_1$-$C_4$alkyl, $R_5$ and $R_6$ are each hydrogen, $R_7$ is a radical of the formula V or VIII, $Q_1$ and $Q_3$ are a direct bond, $R_8$ is hydrogen, $C_1$-$C_4$alkyl, benzyl, allyl, acetyl or —$CH_2CH(OH)R'$, $R_{11}$ is hydrogen and $R_{12}$ is —OH, in particular those in which A is —$CH_2CH(OH)CH_2$—, $R_1$ and $R_2$ are each hydrogen and in particular each methyl, $R_3$ and $R_4$ are each methyl and $R_5$ and $R_6$ are each hydrogen, $R_7$ is a radical of the formula V or VIII, $Q_1$ and $Q_3$ are a direct bond, $R_8$ is methyl, benzyl, allyl or —$CH_2CH(OH)CH_3$, $R_{11}$ is hydrogen and $R_{12}$ is —OH.

The compounds according to the invention can be prepared by methods known per se by reaction of functional derivatives comprising groups of the formula I or II and groups of the formula III. If at least one of $R_3$ to $R_6$ is a radical comprising a group of the formula III, functional derivatives comprising radicals of the formula I or II can also be reacted with any reactive compounds per se which contain no polyalkylpiperidine radicals.

a) Compounds of the formula Ia in which A is —$(CH_2)_mCO$— can be obtained, for example, by reaction of carboxylic acid esters of the formula XX

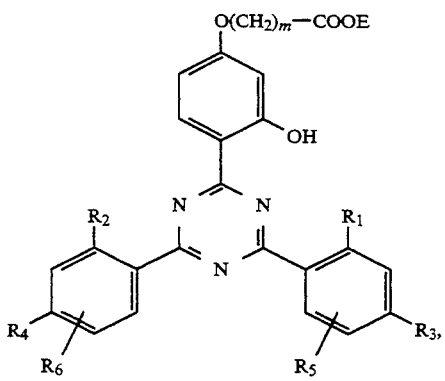

in which E is, for example, $C_1$–$C_4$alkyl, with suitable functional derivatives comprising $R_7$ radicals, such as alcohols or amines. The starting materials of the formula XX can also be obtained in a conventional manner by reaction of the corresponding o-hydroxyphenyl-1,3,5-triazines of the formula XXI

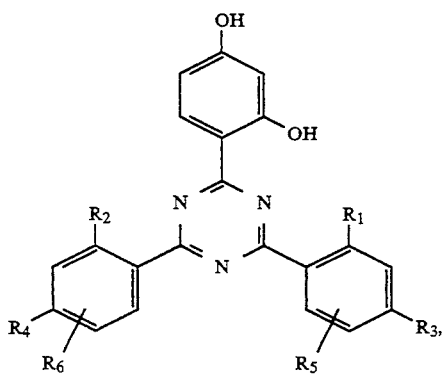

with halocarboxylic acid esters Hal$(CH_2)_m$—COOE in alkaline medium; cf. CH-A 484 695. The compounds of the formula XXI are known compounds and can be prepared by Friedel-Crafts reaction of cyanuric chloride with 1 mol each of a compound of the formula

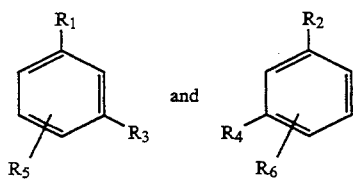

and 1 mol of resorcinol, such as is described, for example, in CH-A 480 091 and CH-A 484 695.

4-Hydroxypiperidine derivatives, 4-aminopiperidine derivatives or piperidine derivatives which are unsubstituted in the 1-position comprising groups of the formula III can also first be reacted with the halocarboxylic acid esters mentioned, after which these are allowed to react in alkaline medium with the o-hydroxyphenyltriazines of the formula XXI.

b) Compounds of the formula Ia where A=—$CH_2CH(R')$—O— can be obtained by reaction of o-hydroxyphenyltriazines of the formula XXI with epoxides

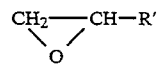

and suitable polyalkylpiperidine derivatives, such as esters, and in particular with chlorotriazines comprising groups of the formula III.

Compounds of the formula Ia where A=—$CH_2CH(R')$—O— can be prepared by allowing an o-hydroxyphenyltriazine of the formula XXI, a dihalide Hal—$CH_2CH(R')$—Hal, preferably with halogen atoms of differing reactivity, for example 1-bromo-2-chloroethane, and a mono- or dihydroxypiperidine derivative comprising at least one group of the formula III to react with one another in any desired sequence per se.

c) Compounds of the formula Ia where A=—$CH_2CH(OH)CH_2$— are obtained, for example, by allowing an o-hydroxyphenyltriazine of the formula XXI, the appropriate epoxide and esters, alcohols or amines comprising at least one group of the formula III to react with one another in any desired sequence per se.

d) Compounds of the formula Ia in which A is a direct bond can be prepared, for example, by reaction of o-hydroxyphenyltriazines of the formula XXI with esters or halides comprising at least one group of the formula III.

e) Compounds of the formula IIa in which B is —$(CH_2)_3CO$— can be obtained, for example, by reaction of compounds of the formula XXII

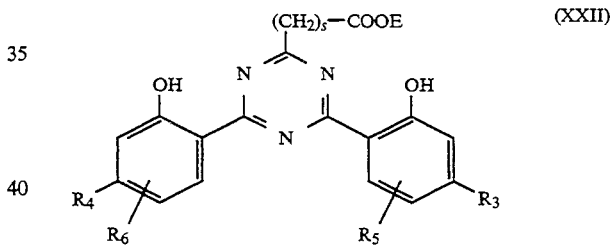

with appropriate functional derivatives comprising $R_7'$ radicals, such as alcohols and amines. Starting materials of the formula XXII can be prepared by the method described in Helv. Chim. Acta 55, 1566–1595 (1972) by reaction of appropriate 2-(2-hydroxyphenyl)-4H-1,3-benzoxazin-4-ones with amidines

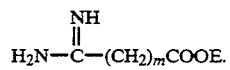

f) Compounds of the formula IIa in which B is —$(CH_2)_r$— can be prepared, for example, by reaction of compounds of the formula XXIIIa or XXIIIb

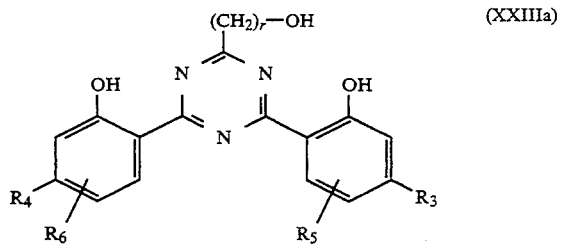

-continued
or

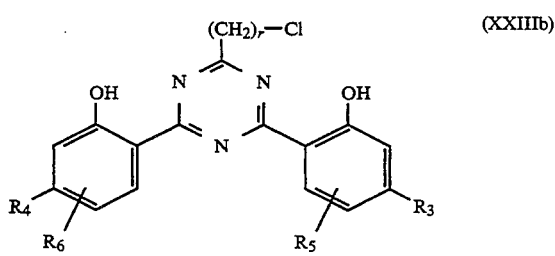

with appropriate functional derivatives comprising R7' radicals, such as esters or alcohols or amines. Starting materials of the formula XXIIIa can be obtained by reaction of the abovementioned 2-(2-hydroxyphenyl)-4H-1,3-benzoxazin-4-ones with amidines

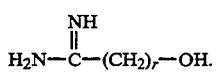

Compounds of the formula XXIIIa can be converted into compounds of the formula XXIIIb in a manner known per se by chlorination, for example with HCl or thionyl chloride.

g) Compounds of the formula IIb in which B is a direct bond can be prepared, for example, by reaction of chlorotriazines of the formula XXIV

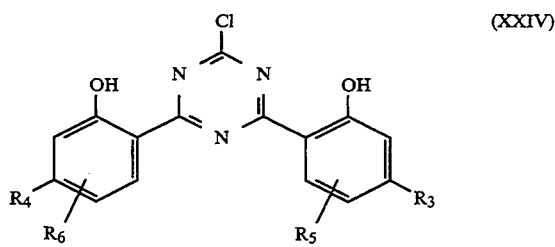

with functional derivatives comprising an R7' radical, such as amines or alcohols. The compounds of the formula XXIV are known and can be obtained by Friedel-Crafts reaction of cyanuric chloride with 1 mol each of an aromatic compound of the formulae

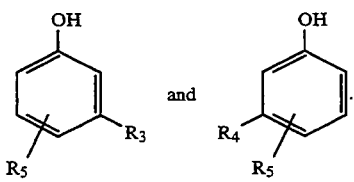

The functional polyalkylpiperidine derivatives needed for the above reaction are known per se or can be prepared by known methods.

If any substituents on the N atom of the piperidine ring contain functional groups, these can be introduced in a manner known per se after the reaction of the triazine derivatives with the piperidine derivatives, for example by hydroxyalkylation.

The compounds according to the invention can be used as stabilisers for organic materials against damage by light, oxygen or heat. The compounds according to the invention are very particularly suitable as light stabilisers. Such materials to be stabilised can be, for example, oils, fats, waxes, cosmetics, biocides or photographic materials. Of particular interest is use in polymeric materials, such as are present in plastics, rubbers, paints or adhesives. Examples of polymers and other substrates which can be stabilised in this manner are the following:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene; as well as polyethylene (which if desired can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low-density polyethylene (LLDPE) and its mixtures with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers ethylene/alkyl acrylate copolymers, ethylene/alkyl methacrylate copolymers, ethylene/vinyl acetate copolymers or ethylene/acrylic acid copolymers and their salts (ionomers) and terpolymers of ethylene with propylene and a diene, such as hexadiene, dicyclopentadiene or ethylidenenorbornene; as well as mixtures of such copolymers with each other and with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers and LLDPE-ethylene/acrylic acid copolymers.

3a. Hydrocarbon resins (for example $C_5$–$C_9$) and hydrogenated modifications thereof (for example tackifier resins).

4. Polystyrene, poly-(p-methylstyrene), poly-(α-methylstyrene).

5. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic anhydride, styrene/acrylonitrile/methyl acrylate; mixtures of high impact strength from copolymers of styrene and another polymer, for example a polyacrylate, a diene polymer or an ethylene/propylene/diene terpolymer; and block copolymers of styrene, for example, styrene/butadiene/styrene, styrene/isoprene/styrene, styrene/ethylene-butylene/styrene or styrene/ethylene-propylene/styrene.

6. Graft copolymers of styrene or α-methylstyrene, for example styrene or polybutadiene; styrene on copolymers of polybutadiene/styrene or polybutadiene/acrylonitrile; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene; styrene and acrylonitrile on ethylene/propylene/diene terpolymers; styrene and acrylonitrile on polyalkyl acrylates or polyalkyl methacrylates; styrene and acrylonitrile on acrylate/butadiene copolymers, as well as mixtures thereof with the copolymers listed under 5), for example those known as so-called ABS, MBS, ASA and AES polymers.

7. Halogen-containing polymers, such as polychloroprene, chlorinated rubber, chlorinated or sulfochlorinated polyethylene, copolymers of ethylene and chlorinated ethylene, epichlorohydrin homo- and copolymers, in particular polymers from halogen-containing vinyl compounds, for example polyvinyl chloride, polyvinylidene chloride, polyvinyl fluoride, polyvinylidene fluoride, as well as copolymers thereof, such as vinyl chloride/vinylidene chloride, vinyl chloride/vinyl acetate or vinylidene chloride/vinyl acetate.

8. Polymers which are derived from α, β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1).

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain comonomers, for example ethylene oxide; polyacetals modified with thermoplastic polyurethanes, acrylates or MBS.

13. Polyphenylene oxides and sulfides, and mixtures thereof with styrene polymers or polyamides.

14. Polyurethanes which are derived from polyethers, polyesters and polybutadienes with terminal hydroxyl groups on the one hand and aliphatic or aromatic polyisocyanates on the other hand, as well as precursors thereof.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained starting from m-xylenediamine and adipic acid; polyamides prepared from hexamethylenediamine and isophthalic and/or terephthalic acid and if desired an elastomer as modifier, for example poly-2,4,4- trimethyl-hexamethylene terephthalamide or poly-m-phenylene-isophthalamide. Block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. In addition, polyamides or copolyamides modified with EPDM or ABS; as well as polyamides condensed during processing (RIM-polyamide systems).

16. Polyureas, polyimides, polyamide-imides and polybenzimidazoles.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, as well as block polyether-esters derived from polyethers having hydroxyl end groups; in addition polyesters modified with polycarbonates or MBS.

18. Polycarbonates and polyester-carbonates.

19. Polysulfones, polyether-sulfones and polyetherketones.

20. Crosslinked polymers which are derived from aldehydes on the one hand and phenols, urea or melamine on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins, derived from substituted acrylic esters, for example epoxy-acrylates, urethane-acrylates or polyester-acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bis-glycidyl ethers or from cycloaliphatic diepoxides.

26. Natural polymers, such as cellulose, natural rubber, gelatin and derivatives thereof which are chemically modified in a polymer-homologous manner, such as cellulose acetates, cellulose propionates and cellulose butyrates, or cellulose ethers, such as methylcellulose; and rosins and their derivatives.

27. Mixtures (polyblends) of the polymers mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6/6 and copolymers, PA/HDPE, PA/PP, PA/PPO.

28. Naturally occurring and synthetic organic materials which are pure monomeric compounds or mixtures of such compounds, for example mineral oils, animal or vegetable fats, oil and waxes, or oils, waxes and fats based on synthetic esters (e.g. phthalates, adipates, phosphates or trimellitates) and also mixtures of synthetic esters with mineral oils in any weight ratio, which mixtures may be used, for example, as spinning preparations, as well as aqueous emulsions thereof.

29. Aqueous emulsions of natural or synthetic rubbers, for example natural latex or latices of carboxylated styrene/butadiene copolymers.

The invention thus also relates to an organic material which is sensitive to light, oxygen and/or heat which contains at least one compound according to the invention. Organic materials which may be mentioned are in particular synthetic polymers, for example thermoplastics or elastomers, in particular the former. Polyolefins are particularly to be emphasised as organic materials.

The use of the compounds according to the invention in coatings of all types is particularly preferred. These can be pigmented or non-pigmented coatings or metal effect coatings. They can contain an organic solvent or be solvent-free or aqueous coatings.

As binders, the coatings can contain at least one of the abovementioned polymers. Examples of coatings containing specific binders are the following:

1. Coatings based on cold- or hot-crosslinkable alkyd, acrylate, polyester, epoxy or melamine resins or mixtures of such resins, if desired with addition of an acidic curing catalyst;
2. Two-component polyurethane coatings based on hydroxyl group-containing acrylate, polyester or polyether resins and aliphatic or aromatic polyisocyanates;
3. Single component polyurethane coatings based on blocked polyisocyanates which are deblocked during stoving;
4. Two-component coatings based on (poly)ketimines and aliphatic or aromatic polyisocyanates;
5. Two-component coatings based on (poly)ketimines and an unsaturated acrylate resin or a polyacetoacetate resin or a methyl methacrylamido glycolate;
6. Two-component coatings based on carboxyl- or amino group-containing polyacrylates and polyepoxides;
7. Two-component coatings based on anhydride group-containing acrylate resins and a polyhydroxy or polyamino component;
8. Two-component coatings based on (poly)oxazolidines and anhydride group-containing acrylate resins or unsaturated acrylate resins or aliphatic or aromatic polyisocyanates.
9. Two-component coatings based on unsaturated polyacrylates and polymalonates;
10. Thermoplastic polyacrylate coatings based on thermoplastic acrylate resins or independently cross-linked acrylate resins in combination with etherified melamine resins;
11. Coating systems based on siloxane-modified acrylate resins;
12. Coating systems based on fluorine-modified acrylate resins, and
13. Coating systems based on allyl glycidyl ethers.

The coatings can also be radiation-curable coatings. In this case, the binding agent is composed of monomeric or oligomeric compounds which contain ethylenic double bonds and change into a crosslinked high molecular weight form as a result of irradiation with actinic light or with electron beams. Usually in this case, the binding agent is a mixture of such compounds.

The coatings can be applied as single layer or two-layer coatings, the stablisers according to the invention preferably being added to the non-pigmented uppermost layer.

The coatings can be applied to the substrates (metal, plastic, wood etc.) by the customary methods, for example by brushing, spraying, pouring, dipping or electrophoresis.

A preferred embodiment of the present invention are thus paints or lacquers (for example automotive lacquers) which contains at least one compound according to the invention. Suitable binders are, for example, those mentioned above.

The amount of compounds according to the invention added depends on the substrate and the demands on its stability. In general 0.01 to 10% by weight, in particular 0.02 to 5% by weight, especially 0.05-3, for example 0.1-2% by weight, thereof are added, relative to the organic material. Mixtures of various compounds according to the definition can also be added.

Incorporation into the organic materials can be carried out, for example, by mixing in the compounds according to the invention and if desired other additives according to the methods customary in industry. Polymers, in particular synthetic polymers, can be incorporated before or during moulding, or by applying the dissolved or dispersed compounds to the polymer, if desired with subsequent evaporation of the solvent. In the case of elastomers, these can also be stabilised as latices. A further possibility for the incorporation of the compounds according to the invention in polymers comprises their addition before or during polymerisation of the corresponding monomers or before crosslinking.

The compounds according to the invention or mixtures thereof can also be added into the plastics to be stabilised in the form of a masterbatch which contains these compounds, for example, in a concentration of 2.5 to 25% by weight.

The incorporation of the compounds according to the invention can expediently be carried out by the following methods:

as an emulsion or dispersion (for example to give latices or emulsion polymers)
as a dry mixture during mixing of additive components or polymer mixtures
by direct addition to the processing apparatus (for example extruders, internal mixers etc.
as a solution or melt.

Incorporation into coatings or coating compositions can also be carried out by customary methods. 0.01 to 5, in particular 0.02 to 3% by weight of compound according to the invention, are expediently added. The addition to the coating formulation can be carried out before, together with or after addition of the binder and, if desired, other components.

In addition to the stabilisers according to the invention, still other stabilisers can be added to the polymers. Examples of these are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'- ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxylbenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl)sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide.

1.10. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'- octoxy, 3',5'-di-tert-amyl and 3',5'-bis(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of variously substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-βcyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl or ethyl ester, nickel complexes of ketoximes, such as of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6,-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrioltriacetate, tetrakis(2,2,6,6-tetramethyl-4-piperidyl) 1,2,3,4-butanetetracarboxylate, 1,1'-(1,2-ethanediyl)-bis(3,3,5,5-tetramethylpiperazinone).

2.7. Oxalic acid diamindes, for example, 4,4'-dioctyloxyoxaniliode, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted oxanilides, and o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-diphosphaspiro[5.5]undecane.

5. Compounds which destroy peroxides, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyracatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticisers, lubricants, emulsifiers, pigments, fluorescent whitening agents, flameproofing agents, antistatic agents and blowing agents.

Other materials customary in plastics and coating technology can additionally be added. Examples of these are fillers and reinforcing agents, pigments, dyes, plasticisers, solvents, lubricants, flow aids, fluorescent brightening agents, nucleating agents, antistatics, flameproofing agents or catalysts (for example acids, metal soaps or slats, amines).

The nature of the further stabilisers added is of course determined by the nature of the substrate to be stabilised and its intended use.

The polymers stabilised in this way can be used in various forms, for example as films, fibres, tapes, moulded parts, profiles, latex, dispersions, coatings or cements.

The compounds according to the invention can also be used as stabilisers, in particular as light stabilisers, for virtually all materials known in reproduction technology, as is described in Research Disclosure 90/31429 [No. 314, pp. 474–480 (1990)].

The present invention thus also relates to recording materials, as described in the abovementioned literature reference, in particular photographic materials, especially colour photographic materials, which contain at least one compound according to the present invention in at least one layer.

The examples which follow illustrate the invention in more detail, without wishing to restrict it to the examples. Therein and also in the remaining description and in the patent claims, parts and percentages are parts by weight and percentages by weight, if not stated otherwise. EA is elemental analysis.

EXAMPLE 1:

14.5 g (0.03 mol) of 2-(2-hydroxy-4-ethoxycarbonylmethoxyphenyl)-4,6-bis(2,4-dimethylphenyl)-1,3,5-triazine (prepared as described in CH-A 484 695, Example 44) are initially introduced into a 100 ml sulfonation flask. 4.65 g (0.03 mol) of 4-hydroxy-2,2,6,6-tetramethylpiperidine and 0.1 g of dibutyltin oxide, as a catalyst, are added to this. The mixture is heated to an internal temperature of 150° C. and a solution of 0.4 g of 4-hydroxy-2,2,6,6-tetramethylpiperidine in 100 ml of toluene is allowed to drip in slowly from a dropping funnel, with stirring, in such a way that a toluene/ethanol mixture is continuously distilled off as a result of the transesterification. After a reaction time of about 6 hours, the thin layer chromatogram (eluent toluene/20% ethanol) no longer shows starting material (hydroxyphenyltriazine). The yellowish melt is then treated with 250 ml of toluene, the solution is cooled, the organic phase is washed twice with 50 ml of warm water each time and the solution is then evaporated on a rotary evaporator. The residue is recrystallised from acetonitrile. The produce (compound 1) is obtained as a beige crystallisate of m.p.: 118°–120° C. (see Table I).

If, instead of 4-hydroxy-2,2,6,6-tetramethylpiperidine, other piperidines substituted in the 1-position are used and the procedure is otherwise exactly the same as described in Example 1, the compounds 2–7 in Table I are obtained. Instead of the bis-xylyl derivative of hydroxyphenyltriazine, the bis-toluyl derivative can also be used (compounds 8–11 in Table I, Example 2).

TABLE I
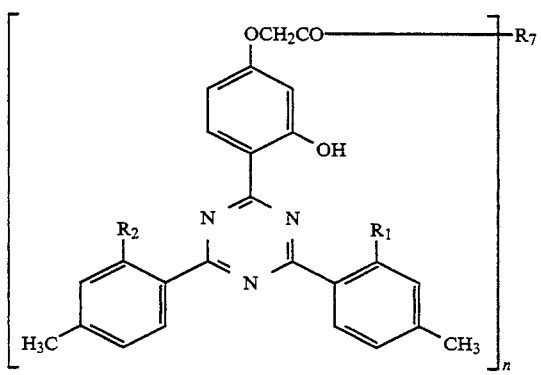
| Compound No. | R7 | n | R1 = R2 | Physical properties |
|---|---|---|---|---|
| 1 | -O-[2,2,6,6-tetramethylpiperidin-4-yl] (NH) | 1 | —CH3 | m.p. 118–120° C. |
| 2 | -O-[1,2,2,6,6-pentamethylpiperidin-4-yl] (N—CH3) | 1 | —CH3 | m.p. 136–138° C. |
| 3 | -O-[1-acetyl-2,2,6,6-tetramethylpiperidin-4-yl] (N—COCH3) | 1 | —CH3 | m.p. 125–128° C. |
| 4 | -O-[1-benzyl-2,2,6,6-tetramethylpiperidin-4-yl] (N—CH2—C6H5) | 1 | —CH3 | m.p. 150–152° C. |
| 5 | -O-[1-allyl-2,2,6,6-tetramethylpiperidin-4-yl] (N—CH2—CH=CH2) | 1 | —CH3 | m.p. 143–145° C. |
| 6 | -O-[2,2,6,6-tetramethylpiperidin-4-yl] (N—CH2CH2O—) | 2 | —CH3 | m.p. 195–197° C. |

TABLE I-continued

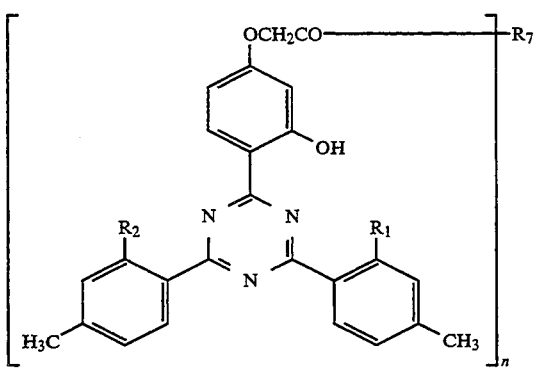

| Compound No. | R7 | n | R1 = R2 | Physical properties |
|---|---|---|---|---|
| 7 | -O-[4-(CH2CH(CH3))-2,2,6,6-tetramethylpiperidin-4-yl-oxy]- (N—CH2CH(CH3)) | 2 | —CH3 | Fp. 110–112° C. |
| 8 | -O-(1-methyl-2,2,6,6-tetramethylpiperidin-4-yl) (N—CH3) | 1 | —H | Fp. 157–160° C. |
| 9 | -O-(2,2,6,6-tetramethylpiperidin-4-yl) (NH) | 1 | —H | Fp. 174–184° C. |
| 10 | -O-(1-allyl-2,2,6,6-tetramethylpiperidin-4-yl) (N—CH2—CH=CH2) | 1 | —H | Fp. 151–154° C. |
| 11 | -O-(1-acetyl-2,2,6,6-tetramethylpiperidin-4-yl) (N—COCH3) | 1 | —H | Fp. 192–194° C. |

EXAMPLE 2:

A suspension of 9.1 g (0.02 mol) of 2-(2-hydroxy-4-ethoxycarbonylmethoxyphenyl)-4,6-bis (4-methylphenyl)-1,3,5-triazine, 4.1 g (0.024 mol) of 4-hydroxy-1,2,2,6,6-pentamethylpiperidine and 0.5 g (2 mmol) of dibutyltin oxide in 90 ml of pure xylene (isomer mixture) is heated to reflux in a 200 ml sulfonation flask. The resultant ethanol is removed using a Dean-Stark water separator. After 21 hours, the reaction mixture is filtered and the solvent is evaporated. The beige solid crude product is recrystallised from 500 ml of petroleum ether (boiling range 110°–140° C.) and dried. 9.9 g (85% of theory) of the compound No. 8 are obtained as a slightly yellow powder; m.p. 157°–160° C.

Compounds 9–11 are obtained in an analogous manner by reaction with other 4-hydroxytetraalkylpiperidines.

EXAMPLE 3:

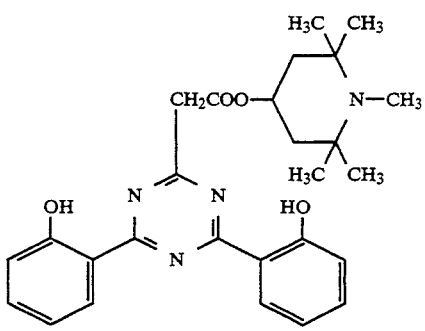

10.5 g of 2-ethoxycarbonylmethyl-4,6-bis(2-hydroxyphenyl)-1,3,5-triazi ne (prepared according to Helv. Chim. Acta, 55, 1585) are heated at 130°–135° C. with 5.6 g of 4-hydroxy-1,2,2,6,6-pentamethylpiperidine and 1.0 g of sodium methoxide in 200 ml of xylene for 6 hours. During the whole reaction time, a mixture of xylene and ethanol is very slowly distilled off. After cooling to room temperature, the reaction solution is washed three times with 50 ml of water each time and then evaporated in vacuo. The ester of the above formula (compound No. 12) having an m.p. of 173° C. is obtained by crystallisation of the residue from ligroin.

EXAMPLE 4:

The following compounds are successively introduced into a 200 ml sulfonation flask; 39.7 g (0.1) mol) of 2-(2,4-dihydroxyphenyl)-4,6-bis(2,4-dimethylphenyl)-1,3,5-triazine, 29.3 g (0.105 mol) of 4-(2-epoxypropyloxy)-N-(propen-2-yl)-2,2,6,6-tetramethylpiperidine, 50 ml of xylene (isomer mixture) and 0.33 g (0.004 mol) of N-methylimidazole. The mixture is heated at 145° C. for 2 hours. A dark yellow reaction solution is formed in this way. After a reaction time of 2 hours, the thin layer chromatogram no longer shows starting material. The reaction mixture is cooled and filtered through 150 g of silica gel, the silica gel is washed with xylene, and the catalyst is extracted by shaking three times with 100 ml of water each time. The organic phase is dried over $Na_2SO_4$ and evaporated. A yellow glassy resin is formed (compound No. 13) (44.5 g=68.4% of theory).

EA: calculated C73.81% H7.74% N8.60% found C73.65% H7.66% N8.50%

Compounds Nos. 14–16 indicated in Table II are obtained in an analogous manner by reaction with other 4-glycidyloxytetramethylpiperidines.

TABLE II

| Compound No. | R | Physical properties/EA |
|---|---|---|
| 14 | [2,2,6,6-tetramethyl-N-methylpiperidinyl] | yellow resin<br>EA: calc. C 73.04% H 7.74% N 8.96%<br>found C 72.75% H 7.89% N 8.82% |
| 15 | [2,2,6,6-tetramethyl-N-benzylpiperidinyl] | yellow resin<br>EA: calc. C 75.39% H 7.47% N 7.97%<br>found C 75.53% H 7.73% N 7.89% |
| 16 | [2,2,6,6-tetramethyl-N-(2-hydroxypropyl)piperidinyl] | yellowish oil<br>EA: calc. C 71.82% H 7.83% N 8.37%<br>found C 71.81% H 7.83% N 8.26% |

EXAMPLE 5:

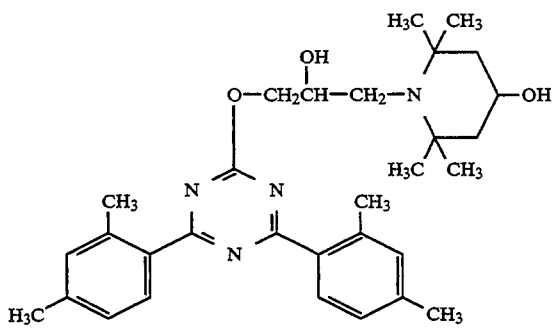

22.4 g (0.105 mol) of 1-(2-epoxypropyl)-4-hydroxy-2,2,6,6-tetramethylpiperidine and 39.7 g (0.1 mol) of 2-(2,4-dihydroxyphenyl)-4,6-bis(2,4-dimethylphenyl)-1,3,5-triazine are initially introduced into a 100 ml sulfonation flask and the mixture is heated to 160° C. 1.6 g of tetrabutylammonium bromide as a catalyst are added under $N_2$ inert gas and the mixture is reacted with stirring and under $N_2$ inert gas at a reaction temperature of 160°–170° C. for 4 hours. The reaction mixture is then cooled and treated with 70 ml of toluene, and the solution is filtered off through Hyflo. The catalyst is then washed with $H_2O$/NaCl solution, the organic phase is dried using $Na_2SO_4$ and the solution is evaporated in a Rotovap. The residue can be recrystallised from toluene. 66.3 g of slightly beige crystals (compound No. 17) of m.p. 185°–187° C. are obtained.

EXAMPLE 6: Testing compounds according to the invention in a two-component polyacrylate coating A hydroxyl group-containing acrylate coating is prepared by mixing the following components:
75 parts of a 60% solution of a hydroxyl group-containing acrylate resin in xylene (Macrynal® SM 510N, Hoechst AG)
15 parts of butylglycol acetate
6.1 parts of an aromatic solvent mixture ((Solvesso® 100, Esso AG)
3.6 parts of methyl isobutyl ketone
0.1 part of zinc octoate (as an 8% solution in toluene)
0.2 part of a flow aid ((Byk® 300, Byk-Chemie).

1.5 parts of the stabilisers indicated below (dissolved in 5–10 arts of xylene) are added to this. This corresponds to 2% stabiliser, relative to solid binder (acrylate+isocyanate). The formulations obtained are mixed with 30 parts of a trimerised diisocyanate (Desmodur® N 75, Bayer AG). The clear lacquer is adjusted for sprayability using xylene. Samples of the lacquer are applied to aluminium sheets, which are coated with a coil coat, an automotive filler based on polyester and a silver metallic base lacquer based on polyester/cellulose acetobutyrate/melamine, and stoved at 80° C. for 45 minutes. A layer thickness of 44–50 μm results.

The sample sheets are weathered in a Xenon-Weatherometer (Atlas Corp., CAM 159, KFA method). The 20° gloss according to DIN 67530 before weathering and after 800, 1600 and 2000 hours and the time (in hours) until crack formation and the appearance of the lacquer according to the TNO crack formation scale, description 353/D, are determined.

| Stabiliser | 20° gloss after ... hours | | | | Crack formation after ... hours/ appearance |
|---|---|---|---|---|---|
| | 0 | 800 | 1600 | 2000 | |
| without stabiliser | 87 | 87 | 2 | — | 1600, matt |
| Stabiliser No. 1 | 87 | 88 | 86 | 80 | 2800, E4b |
| Stabiliser No. 2 | 89 | 89 | 89 | 89 | 2400, E4b |

The good gloss retention and high crack resistance obtainable using the compounds according to the invention are evident from the above data.

What is claimed is:
1. A stabilized composition which comprises
(a) an organic material subject to damage by light oxygen and heat, and
(b) an effective stabilizing amount of at least one compound of formula Ia or IIa

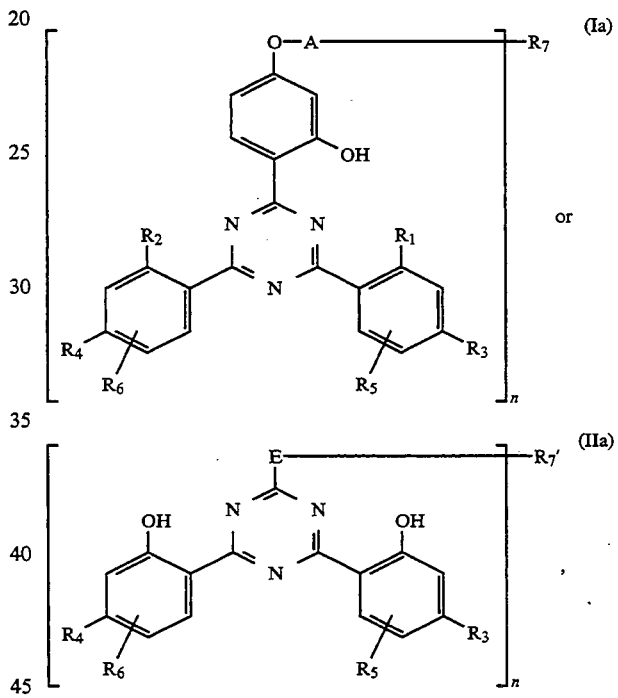

in which n is 1 or 2, $R_1$ and $R_2$ independently of one another are hydrogen, —OH, $C_1$-$C_{12}$alkyl or halogen, $R_3$ and $R_4$ independently of one another are hydrogen, —OH, $C_1$-$C_{12}$alkyl, $C_1$-$C_{18}$alkoxy, halogen or a radical —O—A—$R_7$,$R_5$ and $R_6$ independently of one another are hydrogen, $C_1$-$C_{12}$alkyl, halogen or a radical —O—A—$R_7$, A is a direct bond, —$(CH_2)_m$CO— where m=zero or 1 to 4, —$CH_2CH(R')O$— or —$CH_2C$-$H(OH)CH_2$—, E is a direct bond, —$(CH_2)_s$CO— where s=1 to 4 or —$(CH_2)_r$— where R=1 or 2R' is hydrogen, methyl or phenyl, $R_7$ is a mono- or divalent radical comprising at least one polyalkylpiperidine group of the formula III

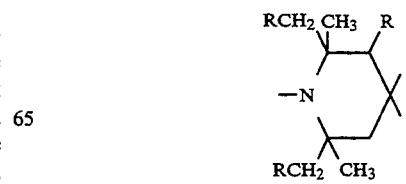

and R7' can have the same meaning as R7 or is the divalent radical of a diamine or diol, where in the latter case at least one of the radicals R3 to R6 in formula IIa is a group —O—A—R7, with the proviso that possible substituents in the 1 position of the piperidine ring are not bonded to the N atom via —O— if A is —CH2CO—.

2. A composition according to claim 1, wherein the organic material is an organic polymer.

3. A composition according to claim 1, wherein the organic material is a paint.

4. A composition according to claim 1, wherein the organic material is a recording material.

5. A composition according to claim 1, wherein polyalkylpiperidine radicals R7 and R7' are a radical of the formulas IV to XIX:

n = 1:

(IV)

(V)

(VI)

(VIIa)

(VIIb)

(VIII)

(IX)

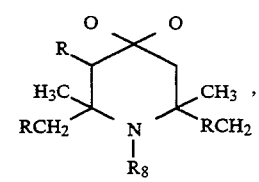

-continued
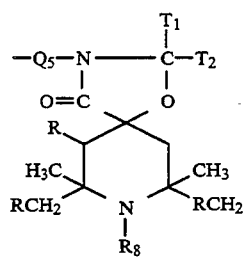
(Xa)
or
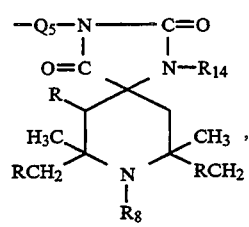
(Xb)
n = 2:
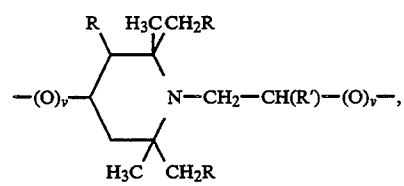
(XI)
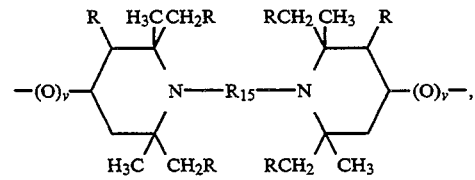
(XII)
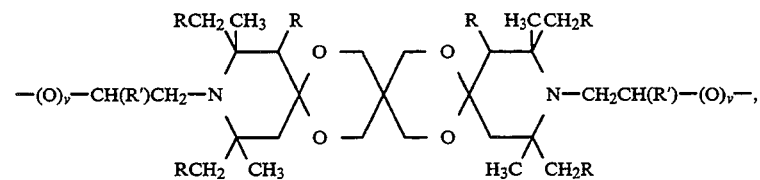
(XIII)
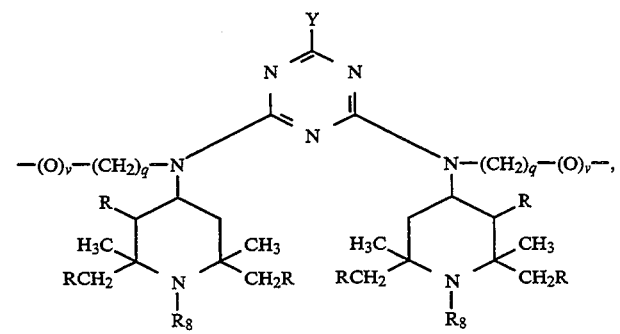
(XIV)
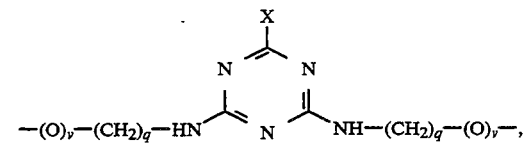
(XV)

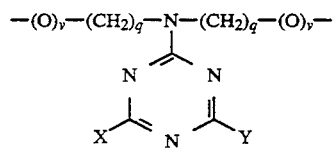 (XVIa)

and

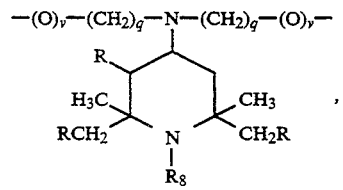 (XVIb)

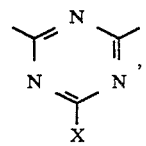 (XVIIa)

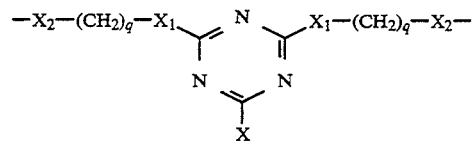 (XVIIb)

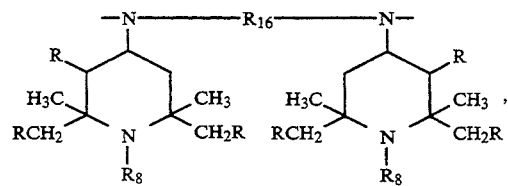 (XVIII)

radicals of the formula XIX in compounds of the formula IIa $-X_1-R_{16}-X_2-$ (XIX), where radicals of the formulae VIIa and XVIIa are present only in compounds of the formula Ia where A=direct bond or —CH$_2$CH(R')O— and radicals of the formulae VIIb and XVIIb are present in compounds of the formula Ia or IIa in which A and E have the meaning indicated in claim 2, but A is not equal to a direct bond or —CH$_2$CH(R')O—, and in which R is methyl or hydrogen, R$_8$ is hydrogen, oxy, C$_1$-C$_{12}$alkyl, C$_1$-C$_{12}$alkoxy, C$_3$-C$_8$alkenyl, C$_3$-C$_8$alkenyloxy, C$_3$-C$_8$alkynyl, C$_5$-C$_6$cycloalkyl, C$_5$-C$_6$cycloalkyloxy, phenyl-C$_1$-C$_4$alkyl, C$_1$-C$_8$alkanoyl, C$_3$-C$_5$alkenoyl, —CH$_2$CH(OH)R' or phenoxy, R' is hydrogen, methyl or phenyl, R$_9$ is hydrogen, C$_1$-C$_{18}$alkyl, allyl, C$_5$-C$_6$cycloalkyl, phenyl-C$_1$-C$_4$alkyl, C$_3$-C$_{18}$alkyl interrupted by one or more —O— or a group of the formula IIIa

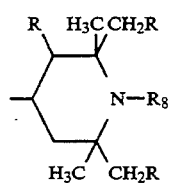 (IIIa)

Q is —O—C$_2$-C$_{12}$alkylene or —NR$_9$—C$_2$-C$_{12}$alkylene if A or E has the meaning indicated, but A is not equal to a direct bond or —CH$_2$CH(R')O—, or in compounds of the formula Ia, Q is C$_2$-C$_{12}$alkylene if A is a direct bond or —CH$_2$CH(R')O—, or is a direct bond if A is —CH$_2$CH(R')O—, Q$_1$ is a direct bond, —O—C$_2$-C$_{12}$alkylene or —NR$_9$—C$_2$-C$_{12}$alkylene if A or E has the meaning indicated, but A is not equal to a direct bond or —CH$_2$CH(R')O—, or in compounds of the formula Ia, Q$_1$ is C$_2$-C$_{12}$alkylene if A is a direct bond or —CH$_2$CH(R')O—, or —OCO—C$_2$-C$_{12}$alkylene if A in compounds of the formula Ia is —CH$_2$CH(OH)CH$_2$— or E in formula IIa is —(CH$_2$)$_r$—, Q$_2$ is a direct bond or —NR$_9$—C$_2$-C$_{12}$alkylene if A or E have the meaning indicated, but A is unequal to a direct bond or —CH$_2$CH(R')O—, or in compounds of the formula Ia, Q$_2$ is —CO—C$_2$-C$_{12}$alkylene if A is a direct bond or —CH$_2$CH(R')O—, or is —OCO—C$_1$-C$_{12}$alkylene or —OCO—C$_1$-C$_{12}$alkylene-CO- if A in formula Ia is —CH$_2$CH(OH)CH$_2$— or E in formula IIa is —(CH$_2$)$_r$—, q is 2-12, and X$_1$ and X$_2$ independently of one another are —O— or —R$_9$N—,

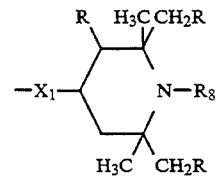

and Y has the same meaning as X or is $C_1$-$C_{18}$alkoxy or —$NR_9R_{10}$, $R_{10}$ can have the same meaning as $R_9$ or, together with $R_9$ and the bonding N atom, forms a 5- or 6-membered heterocyclic ring, $Q_3$ is a direct bond if A in formula Ia is —$CH_2CH(OH)CH_2$— or E in formula IIa is a direct bond or —$(CH_2)_r$—, or $Q_3$ is —$OCH(R')CH_2$— if A or E has the abovementioned meaning, but A is not equal to a direct bond or —$CH_2CH(R')O$—, or $Q_3$ in compounds of the formula Ia is —$CH(R')CH_2$— if A is a direct bond or —$CH_2CH(R')O$—, $R_{11}$ is hydrogen, $C_1$-$C_{18}$alkoxy, $C_3$-$C_8$alkenyloxy or benzyloxy and $R_{12}$ can have the same meaning as $R_{11}$ or $R_{11}$ and $R_{12}$ together are —O—$C_2$-$C_8$alkylene—O—, or if $R_{11}$=H, $R_{12}$ is —OH or —$NR_9$—CO—$R_{13}$, $R_{13}$ is $C_1$-$C_{18}$alkyl, $C_2$-$C_4$alkenyl or phenyl, $Q_4$ is $C_2$-$C_8$alkylene or

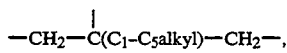

v is the number 1 if A or E have the meaning indicated, but A is not equal to a direct bond or —$CH_2CH(R')O$—, or v in compounds of the formula Ia is zero if a is a direct bond or —$CH_2CH(R')O$—, $Q_5$ is —$OCH_2CH_2$— or —$OCH_2CH(OH)CH_2$— if A or E has the meaning indicated, but A is unequal to a direct bond or —$CH_2CH(R')O$—, or in compounds of the formula Ia, $Q_5$ is —$CO(CH_2)_2$—, or —$CO(CH_2)_3$— if A is a direct bond or —$CH_2CH(R')O$—, $Q_5$ is a direct bond if A is —$CH_2CH(OH)CH_2$—, or $Q_5$ is —$OCO(CH_2)_s$— where s=1–4 if A in formula Ia is —$CH_2CH(OH)CH_2$— or E in formula IIa is —$(CH_2)_r$—, $T_1$ and $T_2$ independently of one another are hydrogen, $C_1$-$C_{18}$alkyl, phenyl-$C_1$-$C_4$alkyl or phenyl or naphthyl which are unsubstituted or substituted by halogen or $C_1$-$C_4$alkyl, or $T_1$ and $T_2$, together with the C atom bonding them, form a $C_5$-$C_{12}$cycloalkane ring, $R_{14}$ is hydrogen, $C_1$-$C_{12}$alkyl, allyl, benzyl or $C_2$-$C_6$alkoxyalkyl, $R_{15}$ is $C_2$-$C_{15}$alkylene which can be interrupted by one or more O atoms, —$CH_2CH=CHCH_2$—, xylylene or —$CH_2CH(OH)CH_2O(CH_2)_{t/2}]_2$ where t=1–6, and $R_{16}$ is $C_2$-$C_{12}$alkylene, phenylene, naphthylene, biphenylene, xylylene, a group —$CH_2CH(OH)CH_2$—, the divalent radical of an aliphatic, cycloaliphatic or aromatic dicarboxylic acid or —CO—.

6. A composition according to claim 1 wherein in component (b), R is hydrogen, R' is hydrogen or methyl and m and s are each the number 1 and $R_1$ and $R_2$, $R_3$ and $R_4$ and also $R_5$ and $R_6$ in pairs each have the same meaning.

7. A composition according to claim 1, where in component (b), $R_1$ and $R_2$ also $R_3$ and $R_4$ in pairs are each hydrogen or $C_1$-$C_4$alkyl and $R_5$ and $R_6$ are each hydrogen.

8. A composition according to claim 1, where in component (b), $R_1$ and $R_2$, in formula Ia are each hydrogen, —OH or methyl, $R_3$ and $R_4$ are each hydrogen, —OH or methyl, and $R_5$ and $R_6$ are each hydrogen.

9. A composition according to claim 1, where in component (b), $R_3$ and $R_4$, in formula IIa are each hydrogen, alkoxy having 1-8 C atoms or a radical —O—A—$R_7'$ and $R_5$ and $R_6$ are each hydrogen.

10. A composition according to claim 5, wherein $R_8$ is hydrogen, oxy, $C_1$-$C_{12}$alkyl, $C_3$-$C_8$alkenyl, $C_3$-$C_8$alkynyl, phenyl-$C_1$-$C_4$alkyl, $C_1$-$C_8$alkanoyl, $C_3$-$C_8$alkenoyl or —$CH_2CH(OH)R'$.

11. A composition according to claim 5, wherein $R_9$ and $R_{10}$ independently of one another are hydrogen, $C_1$-$C_8$alkyl, allyl, cyclohexyl, benzyl or a group of the formula IIIa, in which R is hydrogen and $R_8$ is hydrogen, oxy, $C_1$-$C_{12}$alkyl, $C_3$-$C_8$alkenyl, $C_3$-$C_8$alkynyl, phenyl-$C_1$-$C_4$alkyl, $C_1$-$C_8$alkanoyl, $C_3$-$C_8$alkenoyl or —$CH_2CH(OH)R'$.

12. A composition according to claim 5, wherein A and E, of formula Ia or IIa, are —$CH_2CO$—, $R_1$ and $R_2$ also $R_3$ and $R_4$ in pairs are each hydrogen or $C_1$-$C_4$alkyl, $R_5$ and $R_6$ are each hydrogen, $R_7$ and $R_7'$ are a radical of the formula V or XI, $Q_1$ is a direct bond, $R_8$ is hydrogen, $C_1$-$C_4$alkyl, benzyl, allyl, acetyl or acryloyl, v is the number 1 and R' is hydrogen, methyl or phenyl.

13. A composition according to claim 5, wherein E, of formula IIa, is —$CH_2CO$—, $R_3$ and $R_4$ are each hydrogen or methyl, $R_5$ and $R_6$ are each hydrogen and $R_7'$ is a radical of the formula V, in which $Q_1$ is a direct bond and $R_8$ is hydrogen, methyl, benzyl, allyl or acetyl.

14. A composition according to claim 5, wherein A, of formula Ia, is —$CH_2CO$—, $R_1$ and $R_2$ are each hydrogen or each methyl, $R_3$ and $R_4$ are each methyl and $R_5$ and $R_6$ are each hydrogen and $R_7$ is a radical of the formula V or XI, in which $Q_1$ is a direct bond, $R_8$ is hydrogen, methyl, benzyl, allyl or acetyl, v is the number 1 and R' is hydrogen or methyl.

15. A composition according to claim 5, wherein A, of formula Ia, is —$CH_2CH(OH)CH_2$—, $R_1$ and $R_2$ also $R_3$ and $R_4$ in pairs are each hydrogen or $C_1$-$C_4$alkyl, $R_5$ and $R_6$ are each hydrogen, $R_7$ is a radical of the formula V or VIII, $Q_1$ and $Q_3$ are a direct bond, $R_8$ is hydrogen, $C_1$-$C_4$alkyl, benzyl, allyl, acetyl or —$CH_2CH(OH)R'$, $R_{11}$ is hydrogen and $R_{12}$ is —OH.

16. A composition according to claim 5, wherein A, of formula Ia, is —$CH_2CH(OH)CH_2$—, $R_1$ and $R_2$ are each hydrogen or each methyl, $R_3$ and $R_4$ are each methyl and $R_5$ and $R_6$ are each hydrogen, $R_7$ is a radical of the formula V or VIII, $Q_1$ and $Q_3$ are a direct bond, $R_8$ is methyl, benzyl, allyl, acetyl or —$CH_2CH(OH)CH_3$, $R_{11}$ is hydrogen and $R_{12}$ is —OH.

* * * * *